United States Patent
Walensky et al.

(10) Patent No.: US 11,952,432 B2
(45) Date of Patent: Apr. 9, 2024

(54) CELL-PERMEABLE STAPLED PEPTIDE MODULES FOR CELLULAR DELIVERY

(71) Applicant: Dana-Farber Cancer Institute, Inc., Boston, MA (US)

(72) Inventors: Loren D. Walensky, Newton, MA (US); Rida Mourtada, Brookline, MA (US); Henry D. Herce, Brookline, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 16/961,577

(22) PCT Filed: Feb. 7, 2019

(86) PCT No.: PCT/US2019/016976
§ 371 (c)(1),
(2) Date: Jul. 10, 2020

(87) PCT Pub. No.: WO2019/157131
PCT Pub. Date: Aug. 15, 2019

(65) Prior Publication Data
US 2021/0061856 A1 Mar. 4, 2021

Related U.S. Application Data

(60) Provisional application No. 62/627,566, filed on Feb. 7, 2018.

(51) Int. Cl.
*C07K 7/06* (2006.01)
*A61K 38/00* (2006.01)
*A61K 45/06* (2006.01)

(52) U.S. Cl.
CPC ............... *C07K 7/06* (2013.01); *A61K 38/00* (2013.01); *A61K 45/06* (2013.01); *C07K 2317/55* (2013.01); *C07K 2317/73* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 5,157,021 A | 10/1992 | Balschmidt et al. | |
| 5,446,090 A | 8/1995 | Harris | |
| 5,834,598 A | 11/1998 | Lowman et al. | |
| 6,348,558 B1 | 2/2002 | Harris et al. | |
| 6,576,608 B1 | 6/2003 | Lee et al. | |
| 6,777,388 B1 * | 8/2004 | Grasso .................. | A61K 48/00 514/4.8 |
| 7,166,697 B1 | 1/2007 | Galanis et al. | |
| 7,723,468 B2 | 5/2010 | Daffre et al. | |
| 7,943,129 B2 | 5/2011 | Muruganandam et al. | |
| 8,324,153 B2 | 12/2012 | Debnath et al. | |
| 8,383,107 B2 | 2/2013 | Muruganandam et al. | |
| 8,586,707 B2 | 11/2013 | Lin et al. | |
| 8,592,377 B2 | 11/2013 | Verdine et al. | |
| 8,889,632 B2 | 11/2014 | Bernal et al. | |
| 8,927,500 B2 | 1/2015 | Guerlavais et al. | |
| 8,933,109 B2 | 1/2015 | Quibell et al. | |
| 8,937,154 B2 | 1/2015 | Debnath et al. | |
| 8,957,026 B2 | 2/2015 | Verdine et al. | |
| 9,079,970 B2 | 7/2015 | Walensky et al. | |
| 9,096,684 B2 | 8/2015 | Kawahata et al. | |
| 9,163,330 B2 | 10/2015 | Verdine et al. | |
| 9,175,045 B2 | 11/2015 | Nash et al. | |
| 9,175,047 B2 | 11/2015 | Nash et al. | |
| 9,227,995 B2 | 1/2016 | Jacobsen et al. | |
| 9,296,805 B2 | 3/2016 | Walensky et al. | |
| 9,346,868 B2 | 5/2016 | Witte-Hoffmann | |
| 9,408,885 B2 | 8/2016 | Marine | |
| 9,416,162 B2 | 8/2016 | Bielicki et al. | |
| 9,458,189 B2 | 10/2016 | Verdine et al. | |
| 9,464,125 B2 | 10/2016 | Link et al. | |
| 9,485,202 B2 | 11/2016 | LeCroy et al. | |
| 9,493,510 B2 | 11/2016 | Skerlj et al. | |
| 9,505,801 B2 | 11/2016 | Verdine et al. | |
| 9,505,804 B2 | 11/2016 | Guerlavais et al. | |
| 9,505,816 B2 | 11/2016 | Walensky et al. | |
| 9,517,252 B2 | 12/2016 | Goh et al. | |
| 9,522,947 B2 | 12/2016 | Kawahata et al. | |
| 9,527,896 B2 | 12/2016 | Bernal et al. | |
| 9,556,227 B2 | 1/2017 | Verdine et al. | |
| 9,556,229 B2 | 1/2017 | Ruchala et al. | |
| 9,579,395 B2 | 2/2017 | Divita et al. | |
| 9,617,309 B2 | 4/2017 | Verdine et al. | |
| 9,676,849 B2 | 6/2017 | Farrington et al. | |
| 9,695,224 B2 | 7/2017 | Walensky et al. | |

(Continued)

FOREIGN PATENT DOCUMENTS

| | | |
|---|---|---|
| WO | WO 1999/14259 | 3/1999 |
| WO | WO 1999/34833 | 7/1999 |

(Continued)

OTHER PUBLICATIONS

Balaram, "Non-standard amino acids in peptide design and protein engineering," Curr. Opin. Struct. Biol., 1992, 2:845-51.
Beste et al., "Small antibody-like proteins with prescribed ligand specificities derived from the lipocalin fold," PNAS, 1999, 96(5):1898-1903.
Binz et al., "High-affinity binders selected from designed ankyrin repeat protein libraries," Nat. Biotechnol., 2004, 22(5):575-582.
Bird et al., "Chemical synthesis of hydrocarbon-stapled peptides for protein interaction research and therapeutic targeting," Current Protocols in Chemical Biology, 2011, 3(3):99-117.
Bird et al., "Synthesis and biophysical characterization of stabilized alpha-helices of BCL-2 domains," Methods Enzymol., 2008, 446:369-86.

(Continued)

*Primary Examiner* — Thomas S Heard
(74) *Attorney, Agent, or Firm* — Fish & Richardson P.C.

(57) ABSTRACT

The disclosure relates to cell-permeable stabilized peptide modules and methods of use for e.g., cellular delivery of cargoes.

24 Claims, 12 Drawing Sheets
Specification includes a Sequence Listing.

(56) References Cited

U.S. PATENT DOCUMENTS

| | | | |
|---|---|---|---|
| 9,822,165 | B2 | 11/2017 | Walensky et al. |
| 9,834,581 | B2 | 12/2017 | Divita et al. |
| 2005/0250680 | A1 | 11/2005 | Walensky et al. |
| 2006/0234299 | A1 | 10/2006 | Stemmer et al. |
| 2010/0286057 | A1 | 11/2010 | Walensky et al. |
| 2012/0172285 | A1 | 7/2012 | Walensky et al. |
| 2016/0244494 | A1 | 8/2016 | Verdine et al. |
| 2016/0376336 | A1 | 12/2016 | Link et al. |
| 2017/0015716 | A1 | 1/2017 | Walensky et al. |
| 2017/0066747 | A1 | 3/2017 | Harran et al. |
| 2017/0165320 | A1 | 6/2017 | Vadlamudi et al. |
| 2017/0212125 | A1 | 7/2017 | Nash et al. |
| 2017/0240604 | A1 | 8/2017 | Verdine et al. |
| 2017/0247423 | A1 | 8/2017 | Walensky et al. |
| 2017/0342108 | A1 | 11/2017 | Yu et al. |

FOREIGN PATENT DOCUMENTS

| | | |
|---|---|---|
| WO | WO 2006/055689 | 5/2006 |
| WO | WO 2008/121767 | 10/2008 |
| WO | WO 2010/060112 | 5/2010 |
| WO | WO 2010/068684 | 6/2010 |
| WO | WO 2010/148335 | 12/2010 |
| WO | WO 2015/157508 | 10/2015 |
| WO | WO 2016/115179 | 7/2016 |
| WO | WO 2017/109494 | 6/2017 |

OTHER PUBLICATIONS

Blackwell et al., "Highly Efficient Synthesis of Covalently Cross-Linked Peptide Helices by Ring-Closing Metathesis," Angew Chem. Int. Ed. Engl., 1998, 37(23):3281-4.

Blackwell et al., "Ring-closing metathesis of olefinic peptides: design, synthesis, and structural characterization of macrocyclic helical peptides," J. Org. Chem., 2001, 66(16):5291-5302.

Brunel et al., "Synthesis of constrained helical peptides by thioether ligation: application to analogs of gp41," Chem. Commun., 2005, 20:2552-2554.

Chapman et al., "A highly stable short alpha-helix constrained by a main-chain hydrogen-bond surrogate," J. Am. Chem. Soc., 2004, 126(39):12252-3.

Chin et al., "Design and Evolution of a Miniature Bcl-2 Binding Protein," Angew Chem Int. Ed., 2001, 40(20):3806-9.

Cox et al., "Therapeutic genome editing: prospects and challenges," Nat Med., 2015, 21(2):121-131.

Gunnoo et al., "Bioconjugation—using selective chemistry to enhance the properties of proteins and peptides as therapeutics and carriers," Org. Biomol, Chem., 2016, 14(34):8002-8013.

Haney et al., "Promoting peptide α-helix formation with dynamic covalent oxime side-chain cross-links" Chem. Commun., 2011, 47(39):10915-10917.

Hilinski et al., "Stitched α-Helical Peptides via Bis Ring-Closing Metathesis," J. Am. Chem. Soc., 2014, 136(35):12314-12322.

Horne et al., "Sequence-based design of alpha/beta-peptide foldamers that mimic BH3 domains" Chem., Int. Ed., 2008, 47(15):2853-6.

Jackson et al., "General Approach to the Synthesis of Short α-Helix Peptides," Am. Chem. Soc., 1991, 113:9391-9392.

Kawamoto et al., "Design of triazole-stapled BCL9 α-helical peptides to target the β-catenin/B-cell CLL/lymphoma 9 (BCL9) protein-protein interaction," Journal of Medicinal Chemistry, 2012, 55(3):1137-46.

Kemp et al., "The Structure and Energetics of Helix Formation by Short Templated Peptides in Aqueous Solution. 2. Characterization of the Helical Structure of Ac-Hell-Ala6-OH," J. Am. Chem. Soc., 1996, 118(18):4240-48.

Koppelhus et al., "Cellular delivery of peptide nucleic acid (PNA)," Advanced Drug Delivery Reviews, 2003, 55(2):267-280.

Kumita et al., "Photo-control of helix content in a short peptide," Proc. Natl. Acad. Sci. USA, 2000, 97(8):3803-3808.

Lau et al., "Functionalised Staple Linkages for Modulating the Cellular Activity of Stapled Peptides," Chem. Sci., 2014, 5:1804-1809.

Lau et al., "Peptide stapling techniques based on different macrocyclisation chemistries," Chem. Soc. Rev., 2015, 44(1):91-102.

Madden et al., "Facile synthesis of stapled, structurally reinforced peptide helices via a photoinduced intramolecular 1,3-dipolar cycloaddition reaction," Chem Commun (Camb), 2009, 37:5588-5590.

Madden et al., "Synthesis of cell-permeable stapled peptide dual inhibitors of the p53-Mdm2/Mdmx interactions via photoinduced cycloaddition," Bioorg. Med. Chem. Lett., 2011, 21(5):1472-1475.

Nord et al., "Binding proteins selected from combinatorial libraries of an alpha-helical bacterial receptor domain," Nat. Biotechnol., 1997, 15(8):772-777.

Orner et al., "Toward proteomimetics: terphenyl derivatives as structural and functional mimics of extended regions of an alpha-helix," J. Am. Chem. Soc., 2001, 123(22):5382-3.

Pancer et al., "Somatic diversification of variable lymphocyte receptors in the agnathan sea lamprey," Nature, 2004, 430:174-180.

PCT International Preliminary Report on Patentability in International Appln. No. PCT/US2019/016976, dated Aug. 11, 2020, 8 pages.

PCT International Search Report and Written Opinion in International Appln. No. PCT/US2019/016976, dated Apr. 18, 2019, 11 pages.

Phelan et al., "A General Method for Constraining Short Peptides to an α-Helical Conformation," J. Am. Chem. Soc., 1997, 119(3):455-460.

Schafmeister et al., "An All-Hydrocarbon Cross-Linking System for Enhancing the Helicity and Metabolic Stability of Peptides," J. Am. Chem Soc., 2000, 122(24):5891-92.

Schlenhuber et al., "Lipocalins in drug discovery: From natural ligand-binding proteins to 'anticalins'," Drug Discov. Today, 2005, 10(1):23-33.

Shepard et al., "Single turn peptide alpha helices with exceptional stability in water," J. Am. Chem. Soc., 2005, 127(9):2974-2983.

Spokoyny et al., "A perfluoroaryl-cysteine S(N)Ar chemistry approach to unprotected peptide stapling," J. Am. Chem. Soc., 2013, 135(16):5946-5949.

Synthetic Peptides: A User's Guide, 2nd ed., 1992, Chapter 3, 139 pages.

Walensky et al., "Activation of apoptosis in vivo by a hydrocarbon-stapled BH3 helix," Science, 2004, 305(5689):1466-1470.

Walesnky et al., "Hydrocarbon-stapled peptides: principles, practice, and progress," J. Med. Chem., 2014, 57(15):6275-6288.

Williams et al., "Asymmetric synthesis of monosubstituted and .alpha.,.alpha.-disubstituted .alpha.-amino acids via diastereoselective glycine enolate alkylations," J. Am. Chem. Soc., 1991, 113(24):9276-86.

Williams et al., "Efficient Asymmetric Synthesis of N-tert-Butoxycarbonyl α-Aminoacids Using 4-tert-Butoxycarbonyl-5,6-Diphenylmorpholin-2-one: (R)-(N-tert-Butoxycarbonyl)Allylglycine," Org. Synth., 2003, 80:31-37.

Yang et al., "Calculation of protein conformation from circular dichroism," Methods Enzymol., 1986, 130:208-69.

Zhao et al., "Delivery of cell-penetrating peptide-peptide nucleic acid conjugates by assembly on an oligonucleotide scaffold," Scientific Reports, 2015, 5:17640, 11 pages.

\* cited by examiner

```
                              SEQUENCE LISTING

<160> NUMBER OF SEQ ID NOS: 63

<210> SEQ ID NO 1
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)- 2-(4'-pentenyl)alanine
<220> FEATURE:
<221> NAME/KEY: MOD_RES
<222> LOCATION: (3)..(3)
<223> OTHER INFORMATION: D-Arginine
<220> FEATURE:
<221> NAME/KEY: MOD_RES
<222> LOCATION: (5)..(5)
<223> OTHER INFORMATION: (S)- 2-(4'-pentenyl)alanine

<400> SEQUENCE: 1

Xaa Arg Xaa Arg Xaa Arg
1               5

<210> SEQ ID NO 2
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)- 2-(4'-pentenyl)alanine
<220> FEATURE:
<221> NAME/KEY: MOD_RES
<222> LOCATION: (3)..(3)
<223> OTHER INFORMATION: D-Arginine
<220> FEATURE:
<221> NAME/KEY: MOD_RES
<222> LOCATION: (5)..(5)
<223> OTHER INFORMATION: (S)- 2-(4'-pentenyl)alanine

<400> SEQUENCE: 2

Xaa Arg Xaa Arg Xaa
1               5

<210> SEQ ID NO 3
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)- 2-(4'-pentenyl)alanine
<220> FEATURE:
<221> NAME/KEY: MOD_RES
<222> LOCATION: (3)..(3)
<223> OTHER INFORMATION: D-Arginine
<220> FEATURE:
<221> NAME/KEY: MOD_RES
<222> LOCATION: (5)..(5)
```

```
<223> OTHER INFORMATION: (S)-2-(4'-pentenyl)alanine
<220> FEATURE:
<221> NAME/KEY: MOD_RES
<222> LOCATION: (7)..(7)
<223> OTHER INFORMATION: Norleucine

<400> SEQUENCE: 3

Xaa Arg Xaa Arg Xaa Arg Xaa
1               5

<210> SEQ ID NO 4
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)-2-(4'-pentenyl)alanine
<220> FEATURE:
<221> NAME/KEY: MOD_RES
<222> LOCATION: (3)..(3)
<223> OTHER INFORMATION: D-Arginine
<220> FEATURE:
<221> NAME/KEY: MOD_RES
<222> LOCATION: (5)..(5)
<223> OTHER INFORMATION: (S)-2-(4'-pentenyl)alanine
<220> FEATURE:
<221> NAME/KEY: MOD_RES
<222> LOCATION: (6)..(6)
<223> OTHER INFORMATION: Norleucine

<400> SEQUENCE: 4

Xaa Arg Xaa Arg Xaa Xaa
1               5

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)-2-(4'-pentenyl)alanine
<220> FEATURE:
<221> NAME/KEY: MOD_RES
<222> LOCATION: (3)..(3)
<223> OTHER INFORMATION: D-Arginine
<220> FEATURE:
<221> NAME/KEY: MOD_RES
<222> LOCATION: (5)..(5)
<223> OTHER INFORMATION: (S)-2-(4'-pentenyl)alanine
<220> FEATURE:
<221> NAME/KEY: MOD_RES
<222> LOCATION: (7)..(7)
<223> OTHER INFORMATION: 2-naphthyl-L-alanine

<400> SEQUENCE: 5

Xaa Arg Xaa Arg Xaa Arg Xaa
1               5

<210> SEQ ID NO 6
<211> LENGTH: 6
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)- 2-(4'-pentenyl)alanine
<220> FEATURE:
<221> NAME/KEY: MOD_RES
<222> LOCATION: (3)..(3)
<223> OTHER INFORMATION: D-Arginine
<220> FEATURE:
<221> NAME/KEY: MOD_RES
<222> LOCATION: (5)..(5)
<223> OTHER INFORMATION: (S)- 2-(4'-pentenyl)alanine
<220> FEATURE:
<221> NAME/KEY: MOD_RES
<222> LOCATION: (6)..(6)
<223> OTHER INFORMATION: 2-naphthyl-L-alanine

<400> SEQUENCE: 6

Xaa Arg Xaa Arg Xaa Xaa
1               5

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)- 2-(4'-pentenyl)alanine
<220> FEATURE:
<221> NAME/KEY: MOD_RES
<222> LOCATION: (5)..(5)
<223> OTHER INFORMATION: (S)- 2-(4'-pentenyl)alanine
<220> FEATURE:
<221> NAME/KEY: MOD_RES
<222> LOCATION: (7)..(7)
<223> OTHER INFORMATION: Norleucine

<400> SEQUENCE: 7

Xaa Arg Arg Arg Xaa Arg Xaa
1               5

<210> SEQ ID NO 8
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)- 2-(4'-pentenyl)alanine
<220> FEATURE:
<221> NAME/KEY: MOD_RES
<222> LOCATION: (3)..(3)
<223> OTHER INFORMATION: D-Arginine
<220> FEATURE:
<221> NAME/KEY: MOD_RES
<222> LOCATION: (5)..(5)
<223> OTHER INFORMATION: (S)- 2-(4'-pentenyl)alanine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
```

-continued

```
<222> LOCATION: (9)..(9)
<223> OTHER INFORMATION: Norleucine
<220> FEATURE:
<221> NAME/KEY: MOD_RES
<222> LOCATION: (11)..(11)
<223> OTHER INFORMATION: (S)- 2-(4'-pentenyl)alanine
<220> FEATURE:
<221> NAME/KEY: MOD_RES
<222> LOCATION: (13)..(13)
<223> OTHER INFORMATION: D-Arginine
<220> FEATURE:
<221> NAME/KEY: MOD_RES
<222> LOCATION: (15)..(15)
<223> OTHER INFORMATION: (S)- 2-(4'-pentenyl)alanine

<400> SEQUENCE: 8

Xaa Arg Xaa Arg Xaa Arg Xaa Gly Xaa Arg Xaa Arg Xaa Arg Xaa
1               5                   10                  15

<210> SEQ ID NO 9
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: (S)- 2-(4'-pentenyl)alanine
<220> FEATURE:
<221> NAME/KEY: MOD_RES
<222> LOCATION: (3)..(3)
<223> OTHER INFORMATION: D-Arginine
<220> FEATURE:
<221> NAME/KEY: MOD_RES
<222> LOCATION: (5)..(5)
<223> OTHER INFORMATION: (S)- 2-(4'-pentenyl)alanine
<220> FEATURE:
<221> NAME/KEY: MOD_RES
<222> LOCATION: (7)..(7)
<223> OTHER INFORMATION: Norleucine
<220> FEATURE:
<221> NAME/KEY: MOD_RES
<222> LOCATION: (9)..(9)
<223> OTHER INFORMATION: (S)- 2-(4'-pentenyl)alanine
<220> FEATURE:
<221> NAME/KEY: MOD_RES
<222> LOCATION: (11)..(11)
<223> OTHER INFORMATION: D-Arginine
<220> FEATURE:
<221> NAME/KEY: MOD_RES
<222> LOCATION: (13)..(13)
<223> OTHER INFORMATION: (S)- 2-(4'-pentenyl)alanine
<220> FEATURE:
<221> NAME/KEY: MOD_RES
<222> LOCATION: (15)..(15)
<223> OTHER INFORMATION: Norleucine

<400> SEQUENCE: 9

Xaa Arg Xaa Arg Xaa Arg Xaa Gly Xaa Arg Xaa Arg Xaa Arg Xaa
1               5                   10                  15

<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
```

<223> OTHER INFORMATION: Any non-natural amino acid
<220> FEATURE:
<221> NAME/KEY: SITE
<222> LOCATION: (2)..(4)
<223> OTHER INFORMATION: /note="May be L- or D-Arginine"
<220> FEATURE:
<221> NAME/KEY: MOD_RES
<222> LOCATION: (5)..(5)
<223> OTHER INFORMATION: Any non-natural amino acid
<220> FEATURE:
<221> NAME/KEY: source
<223> OTHER INFORMATION: /note="See specification as filed for detailed description of substitutions and preferred embodiments"

<400> SEQUENCE: 10

Xaa Arg Arg Arg Xaa
1               5

<210> SEQ ID NO 11
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (10)..(10)
<223> OTHER INFORMATION: Cyclobutylalanine
<220> FEATURE:
<221> NAME/KEY: MOD_RES
<222> LOCATION: (11)..(11)
<223> OTHER INFORMATION: (S)-2-(4'-pentenyl)alanine

<400> SEQUENCE: 11

Leu Thr Phe Xaa Glu Tyr Trp Ala Gln Xaa Xaa Ser Ala Ala
1               5                   10

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (2)..(2)
<223> OTHER INFORMATION: (S)-2-(4'-pentenyl)alanine
<220> FEATURE:
<221> NAME/KEY: MOD_RES
<222> LOCATION: (4)..(4)
<223> OTHER INFORMATION: D-Arginine
<220> FEATURE:
<221> NAME/KEY: MOD_RES
<222> LOCATION: (6)..(6)
<223> OTHER INFORMATION: (S)-2-(4'-pentenyl)alanine

<400> SEQUENCE: 12

Xaa Xaa Arg Xaa Arg Xaa Arg
1               5

<210> SEQ ID NO 13

```
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (2)..(2)
<223> OTHER INFORMATION: (S)- 2-(4'-pentenyl)alanine
<220> FEATURE:
<221> NAME/KEY: MOD_RES
<222> LOCATION: (4)..(4)
<223> OTHER INFORMATION: D-Arginine
<220> FEATURE:
<221> NAME/KEY: MOD_RES
<222> LOCATION: (6)..(6)
<223> OTHER INFORMATION: (S)- 2-(4'-pentenyl)alanine

<400> SEQUENCE: 13

Xaa Xaa Arg Xaa Arg Xaa
1               5

<210> SEQ ID NO 14
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (2)..(2)
<223> OTHER INFORMATION: (S)- 2-(4'-pentenyl)alanine
<220> FEATURE:
<221> NAME/KEY: MOD_RES
<222> LOCATION: (4)..(4)
<223> OTHER INFORMATION: D-Arginine
<220> FEATURE:
<221> NAME/KEY: MOD_RES
<222> LOCATION: (6)..(6)
<223> OTHER INFORMATION: (S)- 2-(4'-pentenyl)alanine
<220> FEATURE:
<221> NAME/KEY: MOD_RES
<222> LOCATION: (8)..(8)
<223> OTHER INFORMATION: Norleucine

<400> SEQUENCE: 14

Xaa Xaa Arg Xaa Arg Xaa Arg Xaa
1               5

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
```

```
<222> LOCATION: (2)..(2)
<223> OTHER INFORMATION: (S)- 2-(4'-pentenyl)alanine
<220> FEATURE:
<221> NAME/KEY: MOD_RES
<222> LOCATION: (4)..(4)
<223> OTHER INFORMATION: D-Arginine
<220> FEATURE:
<221> NAME/KEY: MOD_RES
<222> LOCATION: (6)..(6)
<223> OTHER INFORMATION: (S)- 2-(4'-pentenyl)alanine
<220> FEATURE:
<221> NAME/KEY: MOD_RES
<222> LOCATION: (7)..(7)
<223> OTHER INFORMATION: Norleucine

<400> SEQUENCE: 15

Xaa Xaa Arg Xaa Arg Xaa Xaa
1               5

<210> SEQ ID NO 16
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (2)..(2)
<223> OTHER INFORMATION: (S)- 2-(4'-pentenyl)alanine
<220> FEATURE:
<221> NAME/KEY: MOD_RES
<222> LOCATION: (4)..(4)
<223> OTHER INFORMATION: D-Arginine
<220> FEATURE:
<221> NAME/KEY: MOD_RES
<222> LOCATION: (6)..(6)
<223> OTHER INFORMATION: (S)- 2-(4'-pentenyl)alanine
<220> FEATURE:
<221> NAME/KEY: MOD_RES
<222> LOCATION: (8)..(8)
<223> OTHER INFORMATION: 2-naphthyl-L-alanine

<400> SEQUENCE: 16

Xaa Xaa Arg Xaa Arg Xaa Arg Xaa
1               5

<210> SEQ ID NO 17
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (2)..(2)
<223> OTHER INFORMATION: (S)- 2-(4'-pentenyl)alanine
<220> FEATURE:
<221> NAME/KEY: MOD_RES
<222> LOCATION: (4)..(4)
<223> OTHER INFORMATION: D-Arginine
<220> FEATURE:
<221> NAME/KEY: MOD_RES
<222> LOCATION: (6)..(6)
```

```
<223> OTHER INFORMATION: (S)- 2-(4'-pentenyl)alanine
<220> FEATURE:
<221> NAME/KEY: MOD_RES
<222> LOCATION: (7)..(7)
<223> OTHER INFORMATION: 2-naphthyl-L-alanine

<400> SEQUENCE: 17

Xaa Xaa Arg Xaa Arg Xaa Xaa
1               5

<210> SEQ ID NO 18
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (2)..(2)
<223> OTHER INFORMATION: (S)- 2-(4'-pentenyl)alanine
<220> FEATURE:
<221> NAME/KEY: MOD_RES
<222> LOCATION: (6)..(6)
<223> OTHER INFORMATION: (S)- 2-(4'-pentenyl)alanine
<220> FEATURE:
<221> NAME/KEY: MOD_RES
<222> LOCATION: (8)..(8)
<223> OTHER INFORMATION: Norleucine

<400> SEQUENCE: 18

Xaa Xaa Arg Arg Arg Xaa Arg Xaa
1               5

<210> SEQ ID NO 19
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (2)..(2)
<223> OTHER INFORMATION: (S)- 2-(4'-pentenyl)alanine
<220> FEATURE:
<221> NAME/KEY: MOD_RES
<222> LOCATION: (4)..(4)
<223> OTHER INFORMATION: D-Arginine
<220> FEATURE:
<221> NAME/KEY: MOD_RES
<222> LOCATION: (6)..(6)
<223> OTHER INFORMATION: (S)- 2-(4'-pentenyl)alanine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (10)..(10)
<223> OTHER INFORMATION: Norleucine
<220> FEATURE:
<221> NAME/KEY: MOD_RES
<222> LOCATION: (12)..(12)
<223> OTHER INFORMATION: (S)- 2-(4'-pentenyl)alanine
```

```
<220> FEATURE:
<221> NAME/KEY: MOD_RES
<222> LOCATION: (14)..(14)
<223> OTHER INFORMATION: D-Arginine
<220> FEATURE:
<221> NAME/KEY: MOD_RES
<222> LOCATION: (16)..(16)
<223> OTHER INFORMATION: (S)- 2-(4'-pentenyl)alanine

<400> SEQUENCE: 19

Xaa Xaa Arg Xaa Arg Xaa Arg Xaa Gly Xaa Arg Xaa Arg Xaa Arg Xaa
1               5                   10                  15

<210> SEQ ID NO 20
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (2)..(2)
<223> OTHER INFORMATION: (S)- 2-(4'-pentenyl)alanine
<220> FEATURE:
<221> NAME/KEY: MOD_RES
<222> LOCATION: (4)..(4)
<223> OTHER INFORMATION: D-Arginine
<220> FEATURE:
<221> NAME/KEY: MOD_RES
<222> LOCATION: (6)..(6)
<223> OTHER INFORMATION: (S)- 2-(4'-pentenyl)alanine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (10)..(10)
<223> OTHER INFORMATION: (S)- 2-(4'-pentenyl)alanine
<220> FEATURE:
<221> NAME/KEY: MOD_RES
<222> LOCATION: (12)..(12)
<223> OTHER INFORMATION: D-Arginine
<220> FEATURE:
<221> NAME/KEY: MOD_RES
<222> LOCATION: (14)..(14)
<223> OTHER INFORMATION: (S)- 2-(4'-pentenyl)alanine
<220> FEATURE:
<221> NAME/KEY: MOD_RES
<222> LOCATION: (16)..(16)
<223> OTHER INFORMATION: Norleucine

<400> SEQUENCE: 20

Xaa Xaa Arg Xaa Arg Xaa Arg Xaa Gly Xaa Arg Xaa Arg Xaa Arg Xaa
1               5                   10                  15

<210> SEQ ID NO 21
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Norleucine
<220> FEATURE:
```

```
<221> NAME/KEY: MOD_RES
<222> LOCATION: (12)..(12)
<223> OTHER INFORMATION: (S)- 2-(4'-pentenyl)alanine
<220> FEATURE:
<221> NAME/KEY: MOD_RES
<222> LOCATION: (16)..(16)
<223> OTHER INFORMATION: (S)- 2-(4'-pentenyl)alanine
<220> FEATURE:
<221> NAME/KEY: SITE
<222> LOCATION: (18)..(18)
<223> OTHER INFORMATION: /note="TAMRA conjugated to primary amine of K"
<220> FEATURE:
<221> NAME/KEY: MOD_RES
<222> LOCATION: (24)..(24)
<223> OTHER INFORMATION: (S)- 2-(4'-pentenyl)alanine
<220> FEATURE:
<221> NAME/KEY: MOD_RES
<222> LOCATION: (26)..(26)
<223> OTHER INFORMATION: D-Arginine
<220> FEATURE:
<221> NAME/KEY: MOD_RES
<222> LOCATION: (28)..(28)
<223> OTHER INFORMATION: (S)- 2-(4'-pentenyl)alanine
<220> FEATURE:
<221> NAME/KEY: MOD_RES
<222> LOCATION: (30)..(30)
<223> OTHER INFORMATION: Norleucine

<400> SEQUENCE: 21

Xaa Gly Val Ala Asp Leu Ile Lys Lys Phe Glu Xaa Ile Ala Lys Xaa
1               5                   10                  15
Glu Lys Gly Gly Gly Gly Gly Xaa Arg Xaa Arg Xaa Arg Xaa
            20                  25                  30

<210> SEQ ID NO 22
<211> LENGTH: 42
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (12)..(12)
<223> OTHER INFORMATION: Norleucine
<220> FEATURE:
<221> NAME/KEY: MOD_RES
<222> LOCATION: (16)..(16)
<223> OTHER INFORMATION: (S)- 2-(4'-pentenyl)alanine
<220> FEATURE:
<221> NAME/KEY: MOD_RES
<222> LOCATION: (20)..(20)
<223> OTHER INFORMATION: (S)- 2-(4'-pentenyl)alanine
<220> FEATURE:
<221> NAME/KEY: MOD_RES
<222> LOCATION: (32)..(32)
<223> OTHER INFORMATION: R-octenyl alanine
<220> FEATURE:
<221> NAME/KEY: MOD_RES
<222> LOCATION: (38)..(38)
<223> OTHER INFORMATION: Cyclobutylalanine
<220> FEATURE:
<221> NAME/KEY: MOD_RES
<222> LOCATION: (39)..(39)
<223> OTHER INFORMATION: (S)- 2-(4'-pentenyl)alanine

<400> SEQUENCE: 22

Xaa Arg Lys Ala Leu Glu Thr Leu Arg Arg Val Xaa Asp Gly Val Xaa
1               5                   10                  15
```

-continued

Arg Asn His Xaa Thr Ala Phe Gly Gly Gly Gly Leu Thr Phe Xaa
            20                  25                  30

Glu Tyr Trp Ala Gln Xaa Xaa Ser Ala Ala
        35                  40

<210> SEQ ID NO 23
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Norleucine
<220> FEATURE:
<221> NAME/KEY: MOD_RES
<222> LOCATION: (12)..(12)
<223> OTHER INFORMATION: (S)-2-(4'-pentenyl)alanine
<220> FEATURE:
<221> NAME/KEY: MOD_RES
<222> LOCATION: (16)..(16)
<223> OTHER INFORMATION: (S)-2-(4'-pentenyl)alanine

<400> SEQUENCE: 23

Xaa Gly Val Ala Asp Leu Ile Lys Lys Phe Glu Xaa Ile Ala Lys Xaa
1               5                   10                  15

Glu Lys

<210> SEQ ID NO 24
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (11)..(11)
<223> OTHER INFORMATION: Norleucine
<220> FEATURE:
<221> NAME/KEY: MOD_RES
<222> LOCATION: (15)..(15)
<223> OTHER INFORMATION: (S)-2-(4'-pentenyl)alanine
<220> FEATURE:
<221> NAME/KEY: MOD_RES
<222> LOCATION: (19)..(19)
<223> OTHER INFORMATION: (S)-2-(4'-pentenyl)alanine

<400> SEQUENCE: 24

Arg Lys Ala Leu Glu Thr Leu Arg Arg Val Xaa Asp Gly Val Xaa Arg
1               5                   10                  15

Asn His Xaa Thr Ala Phe
            20

<210> SEQ ID NO 25
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Gly Gly Gly Ser
1

-continued

```
<210> SEQ ID NO 26
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Ser Gly Gly Gly
1

<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Gly Gly Gly Ser
1               5

<210> SEQ ID NO 28
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Gly Gly Gly Gly Gly
1               5

<210> SEQ ID NO 29
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ser Gly Gly Gly Gly
1               5

<210> SEQ ID NO 30
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gly Gly Gly Gly Gly Ser
1               5

<210> SEQ ID NO 31
<211> LENGTH: 6
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ser Gly Gly Gly Gly Gly
1               5

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Gly Gly Gly Gly Gly Ser
1               5

<210> SEQ ID NO 33
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ser Gly Gly Gly Gly Gly Gly
1               5

<210> SEQ ID NO 34
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Gly Gly Gly Gly Ser
1               5

<210> SEQ ID NO 35
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Ser Gly Gly Gly Gly
1               5

<210> SEQ ID NO 36
<211> LENGTH: 25
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This region may encompass 0-4 'Gly Gly
      Gly Xaa Xaa' repeating units"
<220> FEATURE:
<221> NAME/KEY: MOD_RES
<222> LOCATION: (4)..(5)
<223> OTHER INFORMATION: Any amino acid
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (14)..(15)
<223> OTHER INFORMATION: Any amino acid
<220> FEATURE:
<221> NAME/KEY: MOD_RES
<222> LOCATION: (19)..(20)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 36

Gly Gly Gly Xaa Xaa Gly Gly Gly Xaa Xaa Gly Gly Gly Xaa Xaa Gly
1               5                   10                  15

Gly Gly Xaa Xaa Gly Gly Gly Gly Ser
            20                  25

<210> SEQ ID NO 37
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (6)..(25)
<223> OTHER INFORMATION: /note="This region may encompass 0-4 'Xaa Gly
      Gly Gly Ser' repeating units"
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (16)..(16)
<223> OTHER INFORMATION: Any amino acid
<220> FEATURE:
<221> NAME/KEY: MOD_RES
<222> LOCATION: (21)..(21)
<223> OTHER INFORMATION: Any amino acid
<220> FEATURE:
<221> NAME/KEY: source
<223> OTHER INFORMATION: /note="See specification as filed for detailed
      description of substitutions and preferred embodiments"

<400> SEQUENCE: 37

Gly Gly Gly Gly Ser Xaa Gly Gly Gly Ser Xaa Gly Gly Gly Ser Xaa
1               5                   10                  15

Gly Gly Gly Ser Xaa Gly Gly Gly Ser
            20                  25
```

```
<210> SEQ ID NO 38
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This region may encompass 0-4 'Gly Gly
      Gly Pro Ser' repeating units"

<400> SEQUENCE: 38

Gly Gly Gly Pro Ser Gly Gly Gly Pro Ser Gly Gly Gly Pro Ser Gly
1               5                   10                  15

Gly Gly Pro Ser Gly Gly Gly Gly Ser
            20                  25

<210> SEQ ID NO 39
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This region may encompass 0-4 'Gly Gly
      Gly Gly Gln' repeating units"

<400> SEQUENCE: 39

Gly Gly Gly Gly Gln Gly Gly Gly Gly Gln Gly Gly Gly Gly Gln Gly
1               5                   10                  15

Gly Gly Gly Gln Gly Gly Gly Gly Ser
            20                  25

<210> SEQ ID NO 40
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This region may encompass 0-4 'Gly Gly
      Gly Gly Ala' repeating units"

<400> SEQUENCE: 40

Gly Gly Gly Gly Ala Gly Gly Gly Gly Ala Gly Gly Gly Gly Ala Gly
1               5                   10                  15

Gly Gly Gly Ala Gly Gly Gly Gly Ser
            20                  25

<210> SEQ ID NO 41
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
```

```
<221> NAME/KEY: SITE
<222> LOCATION: (6)..(25)
<223> OTHER INFORMATION: /note="This region may encompass 0-4 'Pro Gly
      Gly Gly Ser' repeating units"

<400> SEQUENCE: 41

Gly Gly Gly Gly Ser Pro Gly Gly Gly Ser Pro Gly Gly Gly Ser Pro
1               5                   10                  15

Gly Gly Gly Ser Pro Gly Gly Gly Ser
            20                  25

<210> SEQ ID NO 42
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Gly Gly Gly Gly Ala Gly Gly Gly Ala Gly Gly Gly Gly Ser
1               5                   10                  15

<210> SEQ ID NO 43
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Gly Gly Gly Gln Gly Gly Gly Gly Gln Gly Gly Gly Gly Ser
1               5                   10                  15

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Gly Gly Pro Ser Gly Gly Gly Pro Ser Gly Gly Gly Gly Ser
1               5                   10                  15

<210> SEQ ID NO 45
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Gly Gly Gly Gly Ser Pro Gly Gly Gly Ser Pro Gly Gly Gly Ser
1               5                   10                  15

<210> SEQ ID NO 46
<211> LENGTH: 24
<212> TYPE: PRT
<213> ORGANISM: Artificial Sequence
<220> FEATURE:
```

-continued

```
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (12)..(12)
<223> OTHER INFORMATION: Pentenyl alanine or any other
      non-natural amino acid
<220> FEATURE:
<221> NAME/KEY: MOD_RES
<222> LOCATION: (13)..(13)
<223> OTHER INFORMATION: Norleucine
<220> FEATURE:
<221> NAME/KEY: MOD_RES
<222> LOCATION: (16)..(16)
<223> OTHER INFORMATION: Pentenyl alanine or any other
      non-natural amino acid
<220> FEATURE:
<221> NAME/KEY: source
<223> OTHER INFORMATION: /note="See specification as filed for detailed
      description of substitutions and preferred embodiments"

<400> SEQUENCE: 46

Gln Trp Ala Arg Glu Ile Gly Ala Gln Leu Arg Xaa Xaa Ala Asp Xaa
1               5                   10                  15

Leu Asn Ala Gln Tyr Glu Arg Arg
            20

<210> SEQ ID NO 47
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (6)..(6)
<223> OTHER INFORMATION: Pentenyl alanine or any other
      non-natural amino acid
<220> FEATURE:
<221> NAME/KEY: MOD_RES
<222> LOCATION: (10)..(10)
<223> OTHER INFORMATION: Pentenyl alanine or any other
      non-natural amino acid
<220> FEATURE:
<221> NAME/KEY: source
<223> OTHER INFORMATION: /note="See specification as filed for detailed
      description of substitutions and preferred embodiments"

<400> SEQUENCE: 47

Phe Ser Ser Asn Arg Xaa Lys Ile Leu Xaa Arg Thr Gln Ile Leu Asn
1               5                   10                  15

Gln Glu Trp Lys Gln Arg Arg Ile Gln Pro Val
            20                  25

<210> SEQ ID NO 48
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (7)..(7)
<223> OTHER INFORMATION: Pentenyl alanine or any other
      non-natural amino acid
<220> FEATURE:
<221> NAME/KEY: MOD_RES
<222> LOCATION: (11)..(11)
```

```
<223> OTHER INFORMATION: Pentenyl alanine or any other
      non-natural amino acid
<220> FEATURE:
<221> NAME/KEY: source
<223> OTHER INFORMATION: /note="See specification as filed for detailed
      description of substitutions and preferred embodiments"

<400> SEQUENCE: 48

Arg Arg Phe Phe Gly Ile Xaa Leu Thr Asn Xaa Leu Lys Thr Glu Glu
1               5                   10                  15

Gly Asn

<210> SEQ ID NO 49
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (15)..(15)
<223> OTHER INFORMATION: Pentenyl alanine or any other
      non-natural amino acid
<220> FEATURE:
<221> NAME/KEY: MOD_RES
<222> LOCATION: (19)..(19)
<223> OTHER INFORMATION: Pentenyl alanine or any other
      non-natural amino acid
<220> FEATURE:
<221> NAME/KEY: source
<223> OTHER INFORMATION: /note="See specification as filed for detailed
      description of substitutions and preferred embodiments"

<400> SEQUENCE: 49

Arg Lys Ala Leu Glu Thr Leu Arg Arg Val Gly Asp Gly Val Xaa Arg
1               5                   10                  15

Asn His Xaa Thr Ala Phe
            20

<210> SEQ ID NO 50
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Pentenyl alanine or any other
      non-natural amino acid
<220> FEATURE:
<221> NAME/KEY: MOD_RES
<222> LOCATION: (18)..(18)
<223> OTHER INFORMATION: Pentenyl alanine or any other
      non-natural amino acid
<220> FEATURE:
<221> NAME/KEY: MOD_RES
<222> LOCATION: (22)..(22)
<223> OTHER INFORMATION: Norleucine
<220> FEATURE:
<221> NAME/KEY: source
<223> OTHER INFORMATION: /note="See specification as filed for detailed
      description of substitutions and preferred embodiments"

<400> SEQUENCE: 50

Leu Ser Gln Glu Gln Leu Glu His Arg Glu Arg Ser Leu Xaa Thr Leu
1               5                   10                  15
```

```
Arg Xaa Ile Gln Arg Xaa Leu Phe
            20

<210> SEQ ID NO 51
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(4)
<223> OTHER INFORMATION: R-octenyl alanine
<220> FEATURE:
<221> NAME/KEY: MOD_RES
<222> LOCATION: (10)..(10)
<223> OTHER INFORMATION: Cyclobutylalanine
<220> FEATURE:
<221> NAME/KEY: MOD_RES
<222> LOCATION: (11)..(11)
<223> OTHER INFORMATION: Pentenyl alanine or any other
      non-natural amino acid
<220> FEATURE:
<221> NAME/KEY: source
<223> OTHER INFORMATION: /note="See specification as filed for detailed
      description of substitutions and preferred embodiments"

<400> SEQUENCE: 51

Leu Thr Phe Xaa Glu Tyr Trp Ala Gln Xaa Xaa Ser Ala Ala
1               5                   10

<210> SEQ ID NO 52
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (12)..(12)
<223> OTHER INFORMATION: Pentenyl alanine or any other
      non-natural amino acid
<220> FEATURE:
<221> NAME/KEY: MOD_RES
<222> LOCATION: (16)..(16)
<223> OTHER INFORMATION: Pentenyl alanine or any other
      non-natural amino acid
<220> FEATURE:
<221> NAME/KEY: MOD_RES
<222> LOCATION: (17)..(17)
<223> OTHER INFORMATION: Norleucine
<220> FEATURE:
<221> NAME/KEY: source
<223> OTHER INFORMATION: /note="See specification as filed for detailed
      description of substitutions and preferred embodiments"

<400> SEQUENCE: 52

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 53
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
```

```
      Synthetic peptide"
<220> FEATURE:
<221> NAME/KEY: MOD_RES
<222> LOCATION: (9)..(9)
<223> OTHER INFORMATION: Pentenyl alanine or any other
      non-natural amino acid
<220> FEATURE:
<221> NAME/KEY: MOD_RES
<222> LOCATION: (13)..(13)
<223> OTHER INFORMATION: Pentenyl alanine or any other
      non-natural amino acid
<220> FEATURE:
<221> NAME/KEY: source
<223> OTHER INFORMATION: /note="See specification as filed for detailed
      description of substitutions and preferred embodiments"

<400> SEQUENCE: 53

Ile Trp Ile Ala Gln Glu Leu Arg Xaa Ile Gly Asp Xaa Phe Asn Ala
1               5                   10                  15

Tyr Tyr Ala Arg Arg
            20

<210> SEQ ID NO 54
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Pentenyl alanine or any other
      non-natural amino acid
<220> FEATURE:
<221> NAME/KEY: MOD_RES
<222> LOCATION: (15)..(15)
<223> OTHER INFORMATION: Norleucine
<220> FEATURE:
<221> NAME/KEY: MOD_RES
<222> LOCATION: (18)..(18)
<223> OTHER INFORMATION: Pentenyl alanine or any other
      non-natural amino acid
<220> FEATURE:
<221> NAME/KEY: source
<223> OTHER INFORMATION: /note="See specification as filed for detailed
      description of substitutions and preferred embodiments"

<400> SEQUENCE: 54

Asn Leu Trp Ala Ala Gln Arg Tyr Gly Arg Glu Leu Arg Xaa Xaa Asp
1               5                   10                  15

Asp Xaa Phe Val Asp Ser Phe Lys Lys
            20                  25

<210> SEQ ID NO 55
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: Pentenyl alanine or any other
      non-natural amino acid
<220> FEATURE:
<221> NAME/KEY: MOD_RES
<222> LOCATION: (15)..(15)
<223> OTHER INFORMATION: Norleucine
<220> FEATURE:
```

<221> NAME/KEY: MOD_RES
<222> LOCATION: (18)..(18)
<223> OTHER INFORMATION: Pentenyl alanine or any other
      non-natural amino acid
<220> FEATURE:
<221> NAME/KEY: source
<223> OTHER INFORMATION: /note="See specification as filed for detailed
      description of substitutions and preferred embodiments"

<400> SEQUENCE: 55

Asn Leu Trp Ala Ala Gln Arg Tyr Gly Arg Glu Leu Arg Xaa Xaa Ser
1               5                   10                  15

Asp Xaa Phe Val Asp Ser Phe Lys Lys
            20                  25

<210> SEQ ID NO 56
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (9)..(9)
<223> OTHER INFORMATION: Pentenyl alanine or any other
      non-natural amino acid
<220> FEATURE:
<221> NAME/KEY: MOD_RES
<222> LOCATION: (13)..(13)
<223> OTHER INFORMATION: Pentenyl alanine or any other
      non-natural amino acid
<220> FEATURE:
<221> NAME/KEY: MOD_RES
<222> LOCATION: (19)..(19)
<223> OTHER INFORMATION: Norleucine
<220> FEATURE:
<221> NAME/KEY: source
<223> OTHER INFORMATION: /note="See specification as filed for detailed
      description of substitutions and preferred embodiments"

<400> SEQUENCE: 56

Gln Leu Thr Ala Ala Arg Leu Lys Xaa Leu Gly Asp Xaa Leu His Gln
1               5                   10                  15

Arg Thr Xaa Trp Arg
            20

<210> SEQ ID NO 57
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (13)..(13)
<223> OTHER INFORMATION: Pentenyl alanine or any other
      non-natural amino acid
<220> FEATURE:
<221> NAME/KEY: MOD_RES
<222> LOCATION: (17)..(17)
<223> OTHER INFORMATION: Pentenyl alanine or any other
      non-natural amino acid
<220> FEATURE:
<221> NAME/KEY: source
<223> OTHER INFORMATION: /note="See specification as filed for detailed
      description of substitutions and preferred embodiments"

<400> SEQUENCE: 57

```
Ala Glu Leu Glu Val Glu Ser Ala Thr Gln Leu Arg Xaa Phe Gly Asp
1               5                   10                  15

Xaa Leu Asn Phe Arg Gln Lys Leu Leu
            20                  25
```

<210> SEQ ID NO 58
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (11)..(11)
<223> OTHER INFORMATION: Pentenyl alanine or any other non-natural amino acid
<220> FEATURE:
<221> NAME/KEY: MOD_RES
<222> LOCATION: (15)..(15)
<223> OTHER INFORMATION: Pentenyl alanine or any other non-natural amino acid
<220> FEATURE:
<221> NAME/KEY: source
<223> OTHER INFORMATION: /note="See specification as filed for detailed description of substitutions and preferred embodiments"

<400> SEQUENCE: 58

```
Leu Glu Val Glu Ser Ala Thr Gln Leu Arg Xaa Phe Gly Asp Xaa Leu
1               5                   10                  15

Asn Phe Arg Gln Lys Leu
            20
```

<210> SEQ ID NO 59
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (10)..(10)
<223> OTHER INFORMATION: Pentenyl alanine or any other non-natural amino acid
<220> FEATURE:
<221> NAME/KEY: MOD_RES
<222> LOCATION: (14)..(14)
<223> OTHER INFORMATION: Pentenyl alanine or any other non-natural amino acid
<220> FEATURE:
<221> NAME/KEY: source
<223> OTHER INFORMATION: /note="See specification as filed for detailed description of substitutions and preferred embodiments"

<400> SEQUENCE: 59

```
Glu Val Glu Ser Ala Thr Gln Leu Arg Xaa Phe Gly Asp Xaa Leu Asn
1               5                   10                  15

Phe Arg Gln Lys Leu Leu Lys
            20
```

<210> SEQ ID NO 60
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<220> FEATURE:
<221> NAME/KEY: MOD_RES
<222> LOCATION: (7)..(7)
<223> OTHER INFORMATION: Pentenyl alanine or any other
      non-natural amino acid
<220> FEATURE:
<221> NAME/KEY: MOD_RES
<222> LOCATION: (11)..(11)
<223> OTHER INFORMATION: Pentenyl alanine or any other
      non-natural amino acid
<220> FEATURE:
<221> NAME/KEY: source
<223> OTHER INFORMATION: /note="See specification as filed for detailed
      description of substitutions and preferred embodiments"

<400> SEQUENCE: 60

Ile Ala Gln Glu Leu Arg Xaa Ile Gly Asp Xaa Phe Asn Ala Tyr Tyr
1               5                   10                  15

Ala Arg Arg

<210> SEQ ID NO 61
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (5)..(5)
<223> OTHER INFORMATION: R-octenyl alanine
<220> FEATURE:
<221> NAME/KEY: MOD_RES
<222> LOCATION: (11)..(11)
<223> OTHER INFORMATION: Cyclobutylalanine
<220> FEATURE:
<221> NAME/KEY: MOD_RES
<222> LOCATION: (12)..(12)
<223> OTHER INFORMATION: (S)-2-(4'-pentenyl)alanine

<400> SEQUENCE: 61

Xaa Leu Thr Phe Xaa Glu Tyr Trp Ala Gln Xaa Xaa Ser Ala Ala Ala
1               5                   10                  15

Gly Gly Gly Gly Gly Lys
            20

<210> SEQ ID NO 62
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
gcctagttta tcaccaataa t                                          21

<210> SEQ ID NO 63
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<220> FEATURE:
<221> NAME/KEY: MOD_RES
<222> LOCATION: (1)..(1)
<223> OTHER INFORMATION: Beta-Alanine
<220> FEATURE:
<221> NAME/KEY: MOD_RES
<222> LOCATION: (2)..(2)
<223> OTHER INFORMATION: (S)- 2-(4'-pentenyl)alanine
<220> FEATURE:
<221> NAME/KEY: MOD_RES
<222> LOCATION: (4)..(4)
<223> OTHER INFORMATION: D-Arginine
<220> FEATURE:
<221> NAME/KEY: MOD_RES
<222> LOCATION: (6)..(6)
<223> OTHER INFORMATION: (S)- 2-(4'-pentenyl)alanine
<220> FEATURE:
<221> NAME/KEY: MOD_RES
<222> LOCATION: (8)..(8)
<223> OTHER INFORMATION: Norleucine
<220> FEATURE:
<221> NAME/KEY: MOD_RES
<222> LOCATION: (10)..(10)
<223> OTHER INFORMATION: Beta-Alanine

<400> SEQUENCE: 63

Xaa Xaa Arg Xaa Arg Xaa Arg Xaa Gly Xaa Gly Glu Ala Leu Lys Lys
1               5                   10                  15

Ala Leu Arg Arg His Arg Phe Leu Trp Gln Arg Arg Gln Arg Ala
            20                  25                  30
```

CELL-PERMEABLE STAPLED PEPTIDE MODULES FOR CELLULAR DELIVERY

CROSS REFERENCE TO RELATED APPLICATIONS

This application is a U.S. National Stage application of PCT/US2019/016976 filed Feb. 7, 2019, which claims the benefit of U.S. Provisional Application No. 62/627,566, filed on Feb. 7, 2018. The entire contents of the foregoing applications are incorporated herein by reference.

FEDERALLY SPONSORED RESEARCH OR DEVELOPMENT

This invention was made with government support under grant numbers 1R35CA197583 and 1R21CA209358 awarded by The National Institutes of Health. The government has certain rights in the invention.

TECHNICAL FIELD

The disclosure relates to cell-permeable stapled peptide modules and methods of use thereof.

BACKGROUND

The majority of disease targets for drug development and biomarkers reside inside cells. Although there are a variety of methods to develop drugs that bind with strong affinity to intracellular disease targets, a large proportion of such compounds and biologics cannot enter the cells or enter cells with poor efficiency. Thus, there is a need to develop an effective carrier that can transport these compounds to the intracellular target sites.

SUMMARY

The disclosure relates to cell-permeable stabilized peptide modules and their use as carriers for cellular delivery of cargoes. The cell-permeable stabilized peptide can be any stabilized peptide that is permeable to the cell membranes, e.g., internally cross-linked peptides such as stapled peptides, stitched peptides, peptides containing multiple stitches or staples, or peptides that are internally cross-linked by any means. The positions of the peptide involved in the intermolecular cross-link can be joined by a hydrocarbon tether, or a non-hydrocarbon tether (e.g., ether, thioether, ester, amine, amide, triazole, lactam, oxime, disulfide, bis-lactam, or bis-aryl moiety).

In one aspect, the disclosure relates to an internally cross-linked polypeptide, wherein the internally cross-linked polypeptide has at least one staple or stitch, and at least four guanidinium groups or at least four amino groups. In some instances, the internally cross-linked peptide comprises one or more of a hydrocarbon staple, a lactam staple, a uv-cycloaddition staple, a disulfide staple, an oxime staple, a thioether staple, a photoswitchable staple, a double-click staple, a bis-lactam staple, or a bis-arylation staple.

In one aspect, the disclosure relates to an internally cross-linked polypeptide comprising the amino acid sequence of $X_1R_2R_3R_4X_5$ (SEQ ID NO: 10), wherein $R_2$, $R_3$, and $R_4$ are Arg, and $X_1$ and $X_5$ are amino acids that can be joined by an internal staple. In some embodiments, $X_1$ and $X_5$ are non-natural amino acids.

In one aspect, the disclosure relates to an internally cross-linked polypeptide comprising the amino acid sequence of $X_1R_2R_3R_4X_5$ (SEQ ID NO: 10), wherein $R_2$, $R_3$, and $R_4$ are Arg, and $X_1$ and $X_5$ are the staple positions. In some embodiments, the staple is a hydrocarbon staple. In some embodiments, the staple is a non-hydrocarbon staple (e.g., a lactam staple, a uv-cycloaddition staple, a disulfide staple, an oxime staple, a thioether staple, a photoswitchable staple, a double-click staple, a bis-lactam staple, or a bis-arylation staple).

In some embodiments, $X_1$ and $X_5$ are non-natural amino acids and are joined by an internal staple.

In some embodiments, $R_3$ is D-Arginine. In some embodiments, $R_3$ is L-Arginine. In some embodiments, $R_2$ or $R_4$ is L-Arginine.

In some embodiments, $X_1$ or $X_5$ is (S)-2-(4'-pentenyl) alanine, or both $X_1$ and $X_5$ are (S)-2-(4'-pentenyl) alanine.

In some embodiments, the internally cross-linked polypeptide comprises an amino acid sequence selected from the group consisting of SEQ ID NOs: 1, 2, 3, 4, 5, 6, 7, 8, and 9.

In some embodiments, the internally cross-linked polypeptide comprises a localization sequence. In some embodiments, the localization sequence comprises a nuclear localization sequence, a nuclear export sequence, a FC5 single domain antibody sequence, a mitochondria localization sequence, a peroxisome targeting sequence, or an endoplasmic reticulum signal sequence.

In one aspect, the disclosure relates to a fusion polypeptide comprising an internally cross-linked polypeptide comprising the amino acid sequence of $X_1R_2R_3R_4X_5$ (SEQ ID NO: 10), wherein $R_2$, $R_3$, and $R_4$ are Arg, and $X_1$ and $X_5$ are the staple positions. In some embodiments, the staple is a hydrocarbon staple. In some embodiments, the staple is a non-hydrocarbon staple (e.g., a lactam staple, a uv-cycloaddition staple, a disulfide staple, an oxime staple, a thioether staple, a photoswitchable staple, a double-click staple, a bis-lactam staple, or a bis-arylation staple).

In some embodiments, $X_1$ and $X_5$ are non-natural amino acids and are joined by an internal staple.

In some embodiments, $R_3$ is D-Arginine. In some embodiments, $R_3$ is L-Arginine. In some embodiments, $R_2$ or $R_4$ is L-Arginine.

In some embodiments, $X_1$ or $X_5$ is (S)-2-(4'-pentenyl) alanine, or both $X_1$ and $X_5$ are (S)-2-(4'-pentenyl) alanine.

In some embodiments, the internally cross-linked polypeptide comprises an amino acid sequence selected from the group consisting of SEQ ID NOs: 1, 2, 3, 4, 5, 6, 7, 8, and 9. In some embodiments, the internally cross-linked polypeptide comprises an amino acid sequence selected from the group consisting of SEQ ID NOs: 1, 2, 3, 4, 5, 6, 7, 8, and 9 but that differs from SEQ ID NOs: 1, 2, 3, 4, 5, 6, 7, 8, and 9 in the type of staple used (e.g., use of a non-hydrocarbon staple instead of a hydrocarbon staple).

In some embodiments, the fusion polypeptide comprises an scFv antibody, an scFv-Fc fusion, a dAb (domain antibody), a Fab, a Fab', a F(ab')$_2$ fragment, a single chain antibody, a monobody, or a minibody.

In some embodiments, the internally cross-linked polypeptide comprises a tracer (e.g., a fluorescent molecule such as TAMRA, FITC, etc.). Such polypeptides can be used for assessing cellular uptake of the internally cross-linked polypeptide (and its cargo).

In some embodiments, the fusion polypeptide comprises a small molecule drug, a cytokine, an antioxidant, a nucleic acid, a peptide, a peptide nucleic acid (PNA), an antibody, a gene-editing complex, an RNA-editing complex, a stapled peptide, a stitched peptide, or a protein.

In another aspect, the disclosure relates to a compound comprising an internally cross-linked polypeptide and a cargo. In some embodiments, the internally cross-linked polypeptide has the amino acid sequence of $X_1R_2R_3R_4X_5$ (SEQ ID NO: 10), wherein $R_2$, $R_3$, and $R_4$ are Arg, and $X_1$ and $X_5$ are the staple positions. In some embodiments, the staple is a hydrocarbon staple. In some embodiments, the staple is a non-hydrocarbon staple (e.g., a lactam staple, a uv-cycloaddition staple, a disulfide staple, an oxime staple, a thioether staple, a photoswitchable staple, a double-click staple, a bis-lactam staple, or a bis-arylation staple).

In some embodiments, $X_1$ and $X_5$ are non-natural amino acids and are joined by an internal staple, and wherein the cargo is linked to the internally cross-linked polypeptide.

In some embodiments, the cargo is linked to the internally cross-linked polypeptide by a chemical linker. In some embodiments, the cargo is linked to the internally cross-linked polypeptide by a peptide linker.

In some embodiments, $R_3$ is D-Arginine. In some embodiments, $R_3$ is L-Arginine. In some embodiments, $R_2$ or $R_4$ is L-Arginine.

In some embodiments, $X_1$ or $X_5$ is (S) 2-(4'-pentenyl) alanine, or both $X_1$ and $X_5$ are (S) 2-(4'-pentenyl) alanine.

In some embodiments, the cargo comprises an scFv antibody, an scFv-Fc fusion, a dAb (domain antibody), a Fab, a Fab', a F(ab')$_2$ fragment, a single chain antibody, a monobody, a minibody or a nanobody.

In some embodiments, the cargo is a peptide, a stapled peptide, a small molecule, or an antibody or antigen-binding fragment thereof. In some embodiments, the stapled peptide is a stapled BCL-2 family peptide that can either activate or inhibit apoptosis.

In some embodiments, the cargo is an antioxidant, a nucleic acid, a peptide, a peptide nucleic acid (PNA), an antibody, a gene-editing complex, an RNA-editing complex, a protein, a cytokine, an anxiolytic agent, an anticonvulsant, a polynucleotide, or a cytotoxic agent.

In some embodiments, the compound comprises a tracer (e.g., a fluorescent molecule such as TAMRA, FITC, etc.). Such compounds can be used for assessing cellular uptake of the internally cross-linked polypeptide (and its cargo).

In another aspect, the disclosure also relates to a fusion polypeptide comprising a cell-permeable stapled peptide and a therapeutic protein or peptide.

In some embodiments, the cell-permeable stapled peptide is any stapled peptide that is cell-permeable (e.g., entering the cell).

In some embodiments, the cell-permeable stapled peptide is ATSP-7041 (SEQ ID NO: 11) or analog thereof. In some embodiments, the cell-permeable stapled peptide has a sequence that is selected from SEQ ID NOs: 46-60, or the analog thereof.

In some embodiments, the therapeutic protein or peptide is an scFv antibody, an scFv-Fc fusion, a dAb (domain antibody), Fab, Fab' and F(ab')$_2$ fragment, a single chain antibody, a monobody, a minibody, a stapled peptide, a stitched peptide, or a stapled and stitched peptide.

In one aspect, the disclosure also relates to a compound comprising a cell-permeable stapled peptide and a cargo, wherein the cargo is linked to the cell-permeable stapled peptide. In some embodiments, the cell-permeable stapled peptide is any stapled peptide that is cell-permeable.

In some embodiments, the cell-permeable stapled peptide is ATSP-7041 (SEQ ID NO: 11) or analog thereof. In some embodiments, the cell-permeable stapled peptide has a sequence that is selected from SEQ ID NOs: 46-60, or the analog thereof.

In some embodiments, the cargo is linked to the internally cross-linked polypeptide by a chemical linker. In some embodiments, the cargo is linked to the internally cross-linked polypeptide by a peptide linker.

In some embodiments, the cargo comprises an scFv antibody, an scFv-Fc fusion, a dAb (domain antibody), a Fab, a Fab', a F(ab')$_2$ fragment, a single chain antibody, or a minibody.

In some embodiments, the cargo is a stapled peptide, a stitched peptide, a small molecule, or an antibody or antigen-binding fragment thereof.

In some embodiments, the stapled peptide is a stapled BCL-2 family peptide that can either activate or inhibit apoptosis.

In some embodiments, the cargo is an antioxidant, a nucleic acid, a peptide, a peptide nucleic acid (PNA), an antibody, a gene-editing complex, an RNA-editing complex, a protein, a cytokine, an anxiolytic agent, an anticonvulsant, a polynucleotide, or a cytotoxic agent.

In one aspect, the disclosure also provides methods of delivering an agent into a cell. The methods involve the steps of contacting the cell with a compound comprising (1) the agent and (2) a cell-permeable stapled peptide, wherein the agent is linked to the cell-permeable stapled peptide.

In some embodiments, the cell-permeable stapled peptide comprises an internally cross-linked polypeptide comprising the amino acid sequence of $X_1R_2R_3R_4X_5$ (SEQ ID NO: 10), wherein $R_2$, $R_3$, and $R_4$ are Arg, and $X_1$ and $X_5$ are the staple positions. In some embodiments, the staple is a hydrocarbon staple. In some embodiments, the staple is a non-hydrocarbon staple (e.g., a lactam staple, a uv-cycloaddition staple, a disulfide staple, an oxime staple, a thioether staple, a photoswitchable staple, a double-click staple, a bis-lactam staple, or a bis-arylation staple). In some embodiments, $X_1$ and $X_5$ are non-natural amino acids and are joined by an internal staple.

In some embodiments, the cell-permeable stapled peptide comprises the sequence of ATSP-7041 (SEQ ID NO: 11) or analog thereof. In some embodiments, the cell-permeable stapled peptide has a sequence that is selected from SEQ ID NOs: 46-60, or the analog thereof.

In some embodiments, the agent is linked to the internally cross-linked polypeptide by a chemical linker. In some embodiments, the agent is linked to the internally cross-linked polypeptide by a peptide linker.

In some embodiments, the agent is an scFv antibody, an scFv-Fc fusion, a dAb (domain antibody), a Fab, a Fab', a F(ab')$_2$ fragment, a single chain antibody, a monobody, or a minibody.

In some embodiments, the agent is a stapled peptide, a stitched peptide, a small molecule, or an antibody or a fragment thereof.

In some embodiments, the stapled peptide is a stapled BCL-2 family peptide that either activates or inhibits apoptosis.

In some embodiments, the agent is an antioxidant, a nucleic acid, a peptide, a peptide nucleic acid (PNA), an antibody, a gene-editing or RNA-editing complex, a protein, a cytokine, an anxiolytic agent, an anticonvulsant, a polynucleotide, or a cytotoxic agent.

In one aspect, the disclosure relates to methods of administering an agent to a subject. The methods involve administering to a subject in need thereof a compound comprising (1) the agent and (2) a cell-permeable stapled peptide, wherein the agent is linked to the cell-permeable stapled peptide.

In some embodiments, the cell-permeable stapled peptide comprises an internally cross-linked polypeptide comprising the amino acid sequence of $X_1R_2R_3R_4X_5$ (SEQ ID NO: 10), wherein $R_2$, $R_3$, and $R_4$ are Arg, and $X_1$ and $X_5$ are the staple positions. In some embodiments, the staple is a hydrocarbon staple. In some embodiments, the staple is a non-hydrocarbon staple (e.g., a lactam staple, a uv-cycloaddition staple, a disulfide staple, an oxime staple, a thioether staple, a photoswitchable staple, a double-click staple, a bis-lactam staple, or a bis-arylation staple).

In some embodiments, $X_1$ and $X_5$ are non-natural amino acids and are joined by an internal staple.

In some embodiments, the cell-permeable stapled peptide comprises the sequence of ATSP-7041 (SEQ ID NO: 11) or analog thereof. In some embodiments, the cell-permeable stapled peptide has a sequence that is selected from SEQ ID NOs: 46-60, or the analog thereof.

In some embodiments, the agent is linked to the internally cross-linked polypeptide by a chemical linker. In some embodiments, the agent is linked to the internally cross-linked polypeptide by a peptide linker.

In some embodiments, the agent is an scFv antibody, an scFv-Fc fusion, a dAb (domain antibody), a Fab, a Fab', a F(ab')$_2$ fragment, a single chain antibody, a monobody, or a minibody.

In some embodiments, the agent is a stapled peptide, a stitched peptide, a small molecule, or an antibody or antigen-binding fragment thereof.

In some embodiments, the stapled peptide is a stapled BCL-2 family peptide that either activates or inhibits apoptosis.

In some embodiments, the agent is an antioxidant, a nucleic acid, a peptide, a peptide nucleic acid (PNA), an antibody, a gene-editing complex, an RNA-editing complex, a protein, a cytokine, an anxiolytic agent, an anticonvulsant, a polynucleotide, or a cytotoxic agent.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
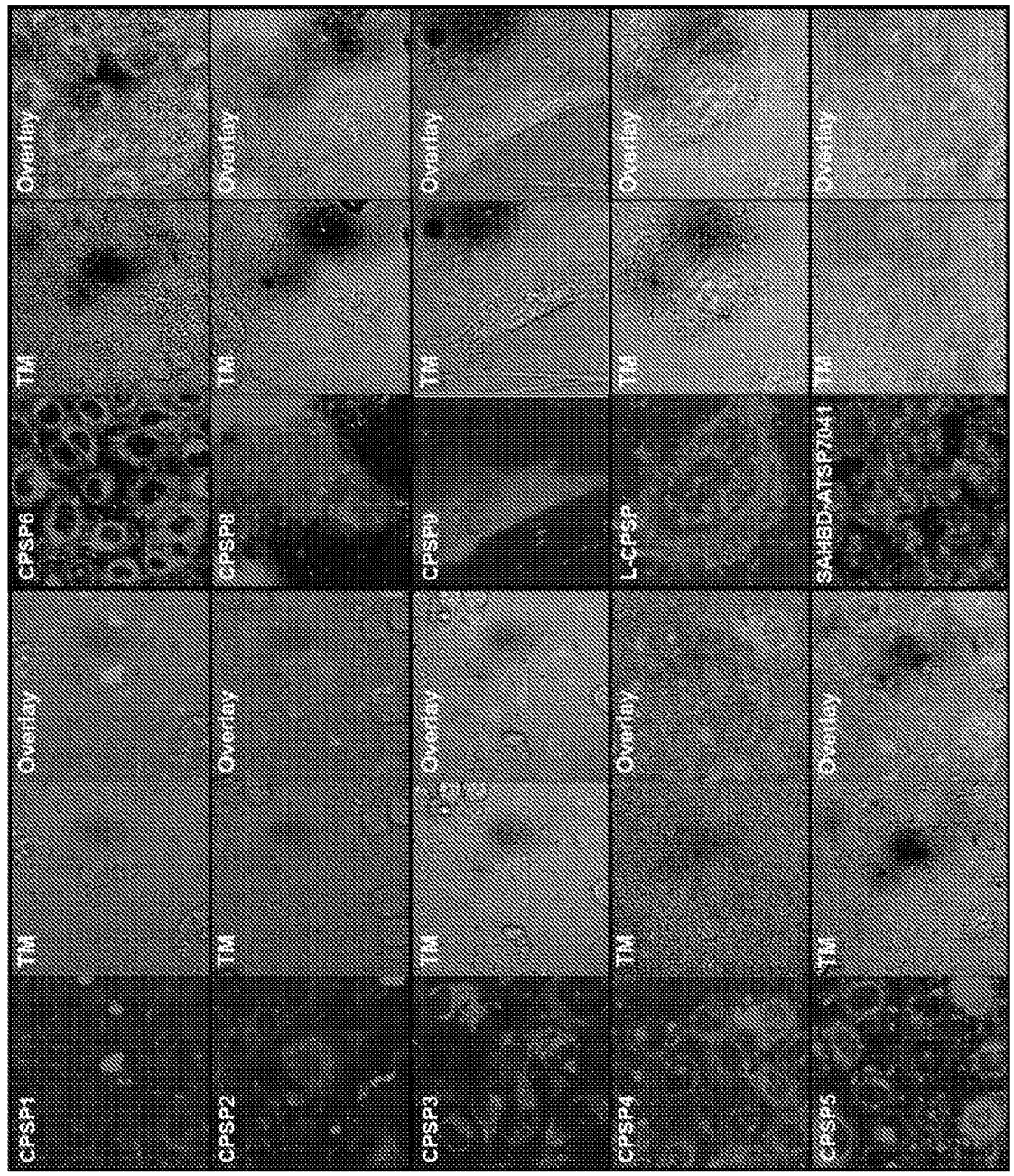
FIG. 1. Cells treated with TAMRA-labeled cell-permeable stapled peptide (CPSP) modules demonstrate robust labeling of cellular compartments (in each 3 panel set: left, fluorescence; middle, transmitted light; right, overlay). The intracellular fluorescence of CPSP modules 1-9, CPSP3 conjugated to an F-actin staining peptide, and a cell penetrant stapled peptide ATSP-7041 conjugated to an MCL-1 SAHB$_D$ stapled peptide are shown.

A large number of agents are developed to target cellular contents, cellular compartments, or specific protein, lipid, nucleic acid or other targets or biomarkers within cells. While these agents can bind to their intracellular targets with strong affinity, many of these compounds, whether they be molecules, proteins, nucleic acids, peptides, nanoparticles, or other intended therapeutic agents or diagnostic markers cannot cross the cell membrane efficiently or at all.

This disclosure provides cell-permeable stapled peptide modules that can serve as efficient carriers of a broad range of cargoes (e.g., diagnostic agents or therapeutic agents) into living cells. These universal carriers can provide cellular penetrance to cell-impermeable compounds or materials, and transport diverse cargoes to intracellular targets for therapeutic and diagnostic purposes. In some embodiments, the carrier is any cell-permeable stapled peptide. In other embodiments, the carrier is an internally cross-linked peptide that contains at least four guanidinium groups or at least four amino groups, wherein the peptide is cross-linked by a hydrocarbon staple or any other staple (e.g., a lactam staple, a uv-cycloaddition staple, a disulfide staple, an oxime staple, a thioether staple, a photoswitchable staple, a double-click staple, a bis-lactam staple, or a bis-arylation staple).

Cell-Permeable Stapled Peptide Modules

The present disclosure provides cell-permeable stapled peptide modules. These peptides can be used as carriers to transport various agents to or within a cell, e.g., to intracellular targets. These cell-permeable peptides are structurally stabilized. Structurally stabilized peptides comprise at least two modified amino acids joined by an internal (intramolecular) cross-link (or staple). Stabilized peptides as described herein include stapled peptides, stitched peptides, peptides containing multiple stitches, peptides containing multiple staples, or peptides containing a mix of staples and stitches, as well as peptides structurally reinforced by other chemical strategies (see. e.g., Balaram P. *Cur. Opin. Struct. Biol.* 1992; 2:845; Kemp D S, et al., *J. Am. Chem. Soc.* 1996; 118:4240; Orner B P, et al., *J. Am. Chem. Soc.* 2001; 123:5382; Chin J W, et al., *Int. Ed.* 2001; 40:3806; Chapman R N, et al., *J. Am. Chem. Soc.* 2004; 126:12252; Horne W S, et al., *Chem., Int. Ed.* 2008; 47:2853; Madden et al., *Chem Commun* (Camb). 2009 Oct. 7; (37): 5588-5590; Lau et al., *Chem. Soc. Rev.*, 2015, 44:91-102; and Gunnoo et al., *Org. Biomol. Chem.*, 2016, 14:8002-8013; all of which are incorporated by reference herein in their entirety). In some instances, the peptides disclosed herein are stabilized by peptide stapling (see, e.g., Walensky, *J. Med. Chem.*, 57:6275-6288 (2014), the contents of which are incorporated by reference herein in its entirety). As used herein, "peptide stapling" is a term coined from a synthetic methodology wherein two side-chains (e.g., cross-linkable side chains) present in a polypeptide chain are covalently joined (e.g., "stapled together") using a ring-closing metathesis (RCM) reaction to form a cross-linked ring (see, e.g., Blackwell et al., *J. Org. Chem.*, 66: 5291-5302, 2001; Angew et al., *Chem. Int. Ed.* 37:3281, 1994). The term "peptide stapling" includes, e.g., the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacing. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed, e.g., in WO 2008/121767 and WO 2010/068684, which are both hereby incorporated by reference in their entirety. In some instances, staples, as used herein, can retain the unsaturated bond or can be reduced. Stapling allows a polypeptide to maintain a constrained or discrete three-dimensional structure or ensemble of structures shape. The crosslinked peptide can increase hydrophobicity, cell permeability, and protease resistance. In some embodiments, the crosslinked peptide has a helical conformation (e.g., alpha helix).

In some embodiments, the cell-permeable stapled peptides can be any stabilized peptides that are permeable to cell membrane (e.g., enter the cell). In some embodiments, the cell-permeable stapled peptides have at least one staple and at least four guanidinium groups or amino groups. In some embodiments, the cell-permeable stapled peptide comprises a tracer (e.g., a fluorescent molecule such as TAMRA, FITC, etc.). Such molecules can be used for assessing cellular uptake of the stapled peptide (and its cargo).

In some embodiments, the cell-permeable stapled peptides of this disclosure have a consensus motif. The sequence for the consensus motif is $X_1R_2R_3R_4X_5$ (SEQ ID NO: 10), wherein $R_2$, $R_3$, and $R_4$ are arginine, and $X_1$ and $X_5$ are staple positions. In certain instances, $X_1$ and/or $X_5$ are non-natural amino acids. The arginine amino acids can be in either the L form or the D form. The staple positions can be joined by an internal hydrocarbon staple. In some embodiments, the staple positions can be joined by a nonhydrocarbon staple (e.g., ether, thioether, ester, amine, or amide, or triazole moiety). In some embodiments, the non-natural amino acids are 2-(4'-pentenyl) alanine, e.g., (S)-2-(4'-pentenyl) alanine. In certain instances, the cell-permeable stapled peptide comprises a lactam staple, a uv-cycloaddition staple, a disulfide staple, an oxime staple, a thioether staple, a photoswitchable staple, a double-click staple, a bis-lactam staple, or a bis-arylation staple.

In some embodiments, the cell-permeable stapled peptides can comprise or consist of a sequence that is set forth in Table 1 (e.g., SEQ ID NOs: 1-9 or SEQ ID NO: 11).

TABLE 1

| Name | Sequence |
|---|---|
| CPSP1 | X R r R X R (SEQ ID NO: 1) |
| CPSP2 | X R r R X (SEQ ID NO: 2) |
| CPSP3 | X R r R X R B (SEQ ID NO: 3) |
| CPSP4 | X R r R X B (SEQ ID NO: 4) |
| CPSP5 | X R r R X R Naph (SEQ ID NO: 5) |
| CPSP6 | X R r R X Naph (SEQ ID NO: 6) |
| CPSP7 | X R R R X R B (SEQ ID NO: 7) |
| CPSP8 | X R r R X R B G B R X R r R X (SEQ ID NO: 8) |
| CPSP9 | X R r R X R B G X R r R X R B (SEQ ID NO: 9) |
| AT5P7041 | L T F 8 E Y W A Q CycB X S A A (SEQ ID NO: 11) |

X: (S)-2-(4'-pentenyl)alanine
Naph: 2-naphthyl-L-alanine
r: D-Arginine
R: L-Arginine
B: Norleucine
CycB: cyclobutylalanine
8: R-octenyl alanine It is of course to be understood that the staple used in the illustrative embodiments of Table 1 are purely exemplary; the peptides of Table 1 can be stapled by any method (e.g., a hydrocarbon staple, a lactam staple, a uv-cycloaddition staple, a disulfide staple, an oxime staple, a thioether staple, a photoswitchable staple, a double-click staple, a bis-lactam staple, or a bis-arylation staple).

In some embodiments, the cell-permeable stapled peptide is a stapled α-helical peptide, e.g., ATSP-7041 (SEQ ID NO: 11), a stapled BH3 peptide of the BCL-2 family, or any other stapled peptide with cell-penetrating capability (e.g., SEQ ID NOs: 46-59). In some embodiments, the cell-permeable stapled peptide has the amino acid sequence set forth in SEQ ID NO:11 with 0 to 5 (e.g., 1, 2, 3, 4, 5) amino substitutions.

These cell-permeable stapled peptides can cross cell membranes and ferry their cargo to various subcellular organelles or structures, e.g., nucleus, nucleolus, mitochondria, endoplasmic reticulum, Golgi apparatus, cytoskeleton, and/or lysosome.

In some embodiments, the cell-permeable stapled peptide is less than 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 amino acids in length. In some embodiments, the cell-permeable stapled peptide is more than 5, 6, 7, 8, 9, 10, 11, 12, 13, 14, 15, 16, 17, 18, 19, 20, 21, 22, 23, 24, 25, 26, 27, 28, 29, 30, 40, or 50 amino acids in length.

Cargos

The cell-permeable stapled peptide can be used as carriers to transport various cargos to intracellular targets. These cargos can be any agent of interest. In some instances, the cargo is a therapeutic agent or a diagnostic agent.

In some embodiments, the cargos include, e.g., small molecules, a nucleic acid (e.g., DNA or RNA), a peptide, or a protein. As used herein, "small molecules" refers to small organic or inorganic molecules of molecular weight below about 3,000 Daltons. In general, small molecules useful for the present disclosure have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

In some instances, the cargo is a pharmaceutically active molecule such as: nerve growth factor (NGF), brain derived neurotrophic factor (BDNF), ciliary neurotrophic factor (CNTF), glial cell-line neurotrophic factor (GDNF), and insulin-like growth factor (IGF). In addition, other compounds that have been shown to have therapeutic potential and may be delivered by the stapled peptides of the disclosure are neuropeptides, including, but not limited to, Substance P, neuropeptide Y, dalargin, alpha-synuclein, vasoactive intestinal peptide (VIP), gamma-amino-butyric acid (GABA), dopamine, cholecystokinin (CCK), endorphins, enkephalins, and thyrotropin releasing hormone (TRH). Further exemplary therapeutics may include cytokines, anxiolytic agents, anticonvulsants, polynucleotides and transgenes, including, for example, small-interfering RNAs.

In some embodiments, the cargo is a cytotoxic agent or a cytostatic agent. In some embodiments, the cargo is an antioxidant (e.g., thiols or ascorbic acid).

In some embodiments, the cargo is a polypeptide or a protein, e.g., growth factors, or cytokines (e.g., IL-1, IL-2, IL-3, IL-4, IL-5, IL-6, IL-7, IL-8, IL-10, IL-11, IL-12, IL-13, IL-17 and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, cytotoxic T lymphocyte antigen 4 (CTLA-4), and interferons such as interferon-α, β, or γ). In some instances, the cargo is a chemokine such as Macrophage inflammatory proteins (MIP-1-α and MIP-1-β), neutrophil chemotactic factor, and RANTES (regulated on activation normally T-cell expressed and secreted).

In some embodiments, the cargo is a hormone, e.g., renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576,608); follicle stimulating hormone (FSH); calcitonin, luteinizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

In certain instances, the cargo is a drug substance used in the treatment, cure, prevention, or diagnosis of disease or used to otherwise enhance physical or mental well-being. Exemplary drugs include analgesics, anesthetics, barbiturates, antihistamines, phenothiazines, butylphenones, opioids, antiemetics, anticholinergic drugs, centrally active antitussive agents; psychiatric drugs; anti-epileptics, anti-Parkinson drugs, antispasticity agents, neuroprotective agents, drugs for the treatment of addiction and drug abuse, autocoids and anti-inflammatory drugs, chemotherapeutic agents, and anti-cancer drugs.

In some embodiments, the cargo comprises an antibody with an antigen-binding site. In one embodiment, the antigen-binding site modulates cellular activation or inhibition (e.g., by binding to a cell surface receptor and resulting in transmission of an activating or inhibitory signal). In one embodiment, the antigen-binding site is capable of initiating transduction of a signal which results in death of the cell (e.g., by a cell signal induced pathway, by complement fixation or exposure to a payload (e.g., a toxic payload) present on the binding molecule), or which modulates a disease or disorder in a subject (e.g., by mediating or promoting cell killing, by promoting lysis of a fibrin clot or promoting clot formation, or by modulating the amount of a substance which is bioavailable). In another embodiment, the antigen-binding site is specific for an antigen targeted for reduction or elimination, e.g., a cell surface antigen or a soluble antigen). In some instances, the cargo is an Fv, a Fd, an scFv antibody, an scFv-Fc fusion, a dAb (domain antibody), a Fab, a Fab', a F(ab')$_2$ fragment, a single chain antibody, a monobody, a minibody, a diabody, a nanobody, or a whole antibody. Exemplary antibodies which can be used or from which binding sites can be derived for use as the cargo of the invention include antibodies that are currently approved by the FDA for use in treatment.

In some instances, the cargo is a binding site derived from a non-immunoglobulin binding molecule. As used herein, the term "non-immunoglobulin binding molecules" are binding molecules whose binding sites comprise an amino acid sequence derived from a polypeptide other than an immunoglobulin. Exemplary non-immunoglobulin binding molecules include Fibronectin binding molecules (e.g., molecules comprising the Fibronectin type I, II, or III domains); Affibodies (see e.g., Nord et al., *Nat. Biotechnol.*, 15: 772-777 (1997); anticalins/lipocalins (see e.g., Schlehuber et al., Drug Discov. Today, 10: 23-33 (2005); Beste et al., PNAS, 96: 1898-1903 (1999); Cysteine-rich domains (e.g., complement components (e.g., C6, C7, C8, C9, and Factor I), serine proteases (e.g., enteropeptidase, matriptase, and corin), transmembrane proteins (e.g., ST7, LRP3, LRPS and LRP6) and endocytic receptors (e.g., Sortilin-related receptor, LDL-receptor, VLDLR, LRP1, LRP2, and ApoER2); repeat proteins such as Designed Ankyrin Repeat Proteins (i.e., a DARPins®, Molecular Partners, Zurich, Switzerland) (see e.g., Binz et al., *Nat. Biotechnol.*, 22: 575-582 (2004)) or leucine-rich repeat proteins (ie., LRRPs) (see e.g., Pancer et al., Nature, 430: 174-180 (2004)); binding sites derived from Src homology domains (e.g. SH2 or SH3 domains), PDZ domains, beta-lactamase, high affinity protease inhibitors, or small disulfide binding protein scaffolds such as scorpion toxins; a binding domain selected from the group consisting of an EGF-like domain, a Kringle-domain, a PAN domain, a Gla domain, a SRCR domain, a Kunitz/Bovine pancreatic trypsin Inhibitor domain, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an Immunoglobulin-like domain, a C-type lectin domain, a MAM domain, a von Willebrand factor type A domain, a Somatomedin B domain, a WAP-type four disulfide core domain, a F5/8 type C domain, a Hemopexin domain, a Laminin-type EGF-like domain, a C2 domain, and a CTLA-4 domain; and Avimers® (Avidia, Inc., Mountain View, CA—see International PCT Publication No. WO 06/055689 and US Patent Pub 2006/0234299), Telobodies® (Biotech Studio, Cambridge, MA), Evibodies® (Evogenix, Sydney, Australia—see U.S. Pat. No. 7,166,697), and Microbodies® (Nascacell Technologies, Munich, Germany).

In some embodiments, the cargo comprises one or more gene-editing components, including e.g., a DNA-editing complex or an RNA-editing complex. For example, the gene-editing complex can include a Cas protein (e.g., a Cas9 protein) and a guide RNA (gRNA) or donor DNA. In some embodiments, the gene-editing complex is a CRISPR/Cas9 complex. In some other embodiments, the gene-editing complex can include, e.g., a TALEN protein, Zinc-finger nuclease (ZFN), mega nuclease, or Cre recombinase. A detailed description of gene-editing components can be found, e.g., in WO2016/115179A1 and Cox et al., *Nat Med* 2015 February; 21(2): 121-131, which are incorporated herein by reference in their entirety.

The present invention is also useful for the delivery of anti-nauseants, relaxants, stimulants, "sense" and "anti-sense" oligonucleotides, cerebral dilators, psychotropics, vascular dilators and constrictors, anti-hypertensives, migraine treatments, hyper- or hypo-glycemic agents, mineral or nutritional agents, anti-obesity drugs, anabolics and anti-asthmatics, anti-inflammatory drugs such as phenylbutazone, indomethacin, naproxen, ibuprofen, flurbiprofen, diclofenac, dexamethasone, prednisone and prednisolone; cerebral vasodilators such as soloctidilum, vincamine, naftidrofuryl oxalate, co-dergocrine mesylate, cyclandelate, papaverine, nicotinic acid, anti-infective agents such as erythromycin stearate, and cephalexin; adrenocorticotropic hormone, adenosine deaminase ribonuclease, alkaline phosphatase, angiotensin, antibodies, arginase, arginine deaminase, asparaginase, caerulein, calcitonin, chymotrypsin, cholecystokinin, clotting factors, dynorphins, endorphins, endorphins, enkephalins, erythropoietin, gastrin-releasing peptide, glucagon, hemoglobin, hypothalamic releasing factors, interferon, katacalcin, motilin, neuropeptide Y, neurotensin, non-naturally occurring opioids, oxytocin, papain, parathyroid hormone, peptides prolactin, soluble CD-4, somatomedin, somatostatin, somatostatin, somatotropin, superoxide dismutase, thyroid stimulating hormone, tissue plasminogen activator, trypsin, vasopressin, and analogues of such peptides, as well as other suitable enzymes, hormones, proteins, polypeptides, enzyme-protein conjugates, antibody-hapten conjugates, viral epitopes, etc.

In some embodiments, the cargo is a stabilized peptide. In certain cases, the stabilized peptide is a stapled peptide. In other instances, the stabilized peptide is a stitched peptide. In certain embodiments, the cargo is a stapled BCL-2 family peptide that can either activate or inhibit apoptosis. Non-limiting examples of stapled BCL-2 family peptides include, e.g., the following:

```
BID BH3 SAHB_A
                                  (SEQ ID NO: 52)
(DIIRNIARHLAX_1VGDX_2BDRSI)

MCL-1 SAHB_D
                                  (SEQ ID NO: 49)
(RKALETLRRVGDGVX_1RNHX_2TAF)

NOXA SAHB_A
                                  (SEQ ID NO: 58)
(LEVESATQLRX_1FGDX_2LNFRQKL)

NOXA_A-3
                                  (SEQ ID NO: 59)
(*EVESATQLRX_1FGDX_2LNFRQKLLK)

BIM SAHB_A1
                                  (SEQ ID NO: 53)
(IWIAQELRX_1IGDX_2FNAYYARR)

BIM SAHB_A1-3
                                  (SEQ ID NO: 60)
(*IAQELRX_1IGDX_2FNAYYARR)
``` wherein B=Norleucine, *=Acrylamide Warhead, X=pentenyl alanine, or any other non-natural amino acid, or other residue that permits stapling, and, in some instances, $X_1$ and $X_2$ are the same (e.g., S-pentenyl alanine).

The cargo may have poor cell permeability. The cell-permeable stapled peptide can increase cell permeability of these cargos, e.g., by at least 10%, 20%, 30%, 40%, 50%, 60%, 70%, 75%, 80%, 90%, 100%, 150%, 200%, 250%, 300%, 400%, or 500%. In some embodiments, the cargo is a therapeutic agent, the cell-permeable stapled peptide can increase the therapeutic effects of the therapeutic agent by at least 20%, 50%, 60%, 70%, 80%, 90%, 100%, 150%, 200%, 250%, 300%, 400%, or 500%. In some embodiments, the cargo is a diagnostic agent (e.g., fluorescent dye). The cell-permeable stapled peptide can increase the signal of the biomarker by at least 20%, 50%, 60%, 70%, 80%, 90%, 100%, 150%, 200%, 250%, 300%, 400%, or 500%.

In some embodiments, the cell-permeable stapled peptide (or the cargo) can be further linked to a localization sequence, e.g., a nuclear localization sequence, a nuclear export sequence, a blood-brain barrier (BBB) transmigrating agent such as an FC5 single domain antibody sequence, FC7, or FC44 (see, U.S. Pat. No. 7,943,129 which is incorporated by reference herein in its entirety), a mitochondria localization sequence, a peroxisome targeting sequence, and/or an endoplasmic reticulum signal sequence. Once the cargos cross cell membranes, the localization sequence can deliver the cargo to the desired target site (e.g., nuclear or mitochondria).

In some embodiments, the localization sequence is an FC5 single heavy domain antibody. The FC5 single heavy domain antibody can bind to TMEM30A (CDC-50A) and can greatly enhance the transport across the blood brain barrier (BBB). The sequence and the methods of use of the FC5 single heavy domain antibody is described e.g., in U.S. Pat. Nos. 8,383,107 and 9,676,849, which are incorporated herein by reference in its entirety.

In some embodiments, the sequence of the cell-permeable stapled peptide itself is a localization sequence. For example, CPSP3 can target mitochondria, and can be used to deliver various agents to mitochondria. In other examples, CPSPs accumulate in the cytosol, nucleus, nucleolus, endosomes, lysosomes, and/or actin filaments and can deliver various agents to these locations.

In some embodiments, the cargo is a polypeptide or the analogue thereof. The polypeptide or an analogue thereof can be less than 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900 or 1000 amino acids in length. In some embodiments, the polypeptide is more than 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500 amino acids in length.

Linkers

The cargos and the cell-permeable stapled peptide can be tethered together by a linker. There is no particular limitation on the linkers that can be used in the constructs described above. The linker can be a chemical bond (e.g., a covalent bond), a small molecule, an amino acid (e.g., glycine, serine, beta-alanine), or a peptide linker (e.g., Gly linkers, Gly-Ser linkers).

In some embodiments, the linker is a beta-alanine. The beta-alanine can serve as a spacer between the cell-permeable stapled peptide and the cargo (e.g., a fluorescent dye such as 5-(and-6)-Carboxytetramethylrhodamine (TAMRA)), so the cell-permeable stapled peptide does not interfere with the cargo's activity.

In some embodiments, the linker is an amino acid such as amino-propionic-acid, amino-butanoic-acid, amino-pentanoic-acid, or amino-hexanoic-acid. In some embodiments, the linker is an oligoethylene glycol, i.e., $NH_2-(CH_2-CH_2-O)_x-CH_2-CH_2-COOH$. In some embodiments, the linker is a peptide linker. In some embodiments, any arbitrary single-chain peptide comprising about one to 30 residues (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acids) can be used as a linker. In other embodiments, the linker is 10 to 20, 10 to 30, 10 to 40, 10 to 50, 10 to 60, 10 to 70, 10 to 80, 10 to 90, 10 to 100, 10 to 144, or 10 to 150 amino acids in length. In certain instances, the linker contains only glycine and/or serine residues. Examples of such peptide linkers include, e.g.:

Gly, Ser;
Gly Ser;
Gly Gly Ser;
Ser Gly Gly;
Gly Gly Gly Ser (SEQ ID NO: 25);
Ser Gly Gly Gly (SEQ ID NO: 26);
Gly Gly Gly Gly Ser (SEQ ID NO: 27);
Gly Gly Gly Gly Gly (SEQ ID NO:28);
Ser Gly Gly Gly Gly (SEQ ID NO: 29);
Gly Gly Gly Gly Gly Ser (SEQ ID NO: 30);
Ser Gly Gly Gly Gly Gly (SEQ ID NO: 31);
Gly Gly Gly Gly Gly Gly Ser (SEQ ID NO: 32);
Ser Gly Gly Gly Gly Gly Gly (SEQ ID NO: 33);
(Gly Gly Gly Gly Ser)$_n$ (SEQ ID NO: 34), wherein n is an integer of one or more; and
(Ser Gly Gly Gly Gly)$_n$ (SEQ ID NO: 35), wherein n is an integer of one or more.

In some instances, the linker has the amino acid sequence of SEQ ID NO: 28.

In other embodiments, the linker peptides are modified such that the amino acid sequence GSG (that occurs at the junction of traditional Gly/Ser linker peptide repeats) is not present. For example, the peptide linker comprise an amino acid sequence selected from the group consisting of: (GGGXX)$_n$GGGGS (SEQ ID NO: 36) and GGGGS (XGGGS)$_n$(SEQ ID NO: 37), where X is any amino acid that can be inserted into the sequence and not result in a polypeptide comprising the sequence GSG, and n is 0 to 4. In one embodiment, the sequence of a linker peptide is (GGGX$_1$X$_2$)$_n$GGGGS and X$_1$ is P and X$_2$ is S and n is 0 to 4 (SEQ ID NO: 38). In another embodiment, the sequence of a linker peptide is (GGGX$_1$X$_2$)$_n$GGGGS and X$_1$ is G and X$_2$ is Q and n is 0 to 4 (SEQ ID NO: 39). In another embodiment, the sequence of a linker peptide is (GGGX$_1$X$_2$)$_n$GGGGS and X$_1$ is G and X$_2$ is A and n is 0 to 4 (SEQ ID NO: 40). In yet another embodiment, the sequence of a linker peptide is GGGGS(XGGGS)$_n$, and X is P and n is 0 to 4 (SEQ ID NO: 41). In one embodiment, a linker peptide of the invention comprises or consists of the amino acid sequence (GGGGA)$_2$GGGGS (SEQ ID NO: 42). In another embodiment, a linker peptide comprises or consists of the amino acid sequence (GGGGQ)$_2$GGGGS (SEQ ID NO: 43). In yet another embodiment, a linker peptide comprises or consists of the amino acid sequence (GGGPS)$_2$GGGGS (SEQ ID NO:44). In a further embodiment, a linker peptide comprises or consists of the amino acid sequence GGGGS(PGGGS)$_2$ (SEQ ID NO: 45).

In certain embodiments, the linker is a synthetic compound linker (chemical cross-linking agent). Examples of cross-linking agents include, e.g., N-hydroxysuccinimide (NHS), and disuccinimidylsuberate (DSS), bis(sulfosuccinimidyl)suberate (BS3), dithiobis(succinimidylpropionate) (DSP), dithiobis(sulfosuccinimidylpropionate) (DTSSP), ethyleneglycol bis(succinimidylsuccinate) (EGS), ethyleneglycol bis(sulfosuccinimidylsuccinate) (sulfo-EGS), disuccinimidyl tartrate (DST), disulfosuccinimidyl tartrate (sulfo-DST), bis[2-(succinimidooxycarbonyloxy)ethyl] sulfone (BSOCOES), and bis[2-(sulfosuccinimidooxycarbonyloxy)ethyl]sulfone (sulfo-BSOCOES).

Stabilized Peptides

The cell-permeable stapled peptide described herein is a stabilized peptide, wherein two or more side-chains of the peptide are covalently joined. The cell-permeable stapled peptide can also be linked to other stabilized peptides and be used to transport them into cells.

Stabilized peptides include, e.g., stapled peptides, stitched peptides, peptides containing multiple stitches, peptides containing multiple staples, or peptides containing a mix of staples and stitches, as well as peptides structurally reinforced by other chemical strategies (see. e.g., Balaram P. *Cur. Opin. Struct. Biol.* 1992; 2:845; Kemp D S, et al., *J. Am. Chem. Soc.* 1996; 118:4240; Orner B P, et al., *J. Am. Chem. Soc.* 2001; 123:5382; Chin J W, et al., *Int. Ed.* 2001; 40:3806; Chapman R N, et al., *J. Am. Chem. Soc.* 2004; 126:12252; Horne W S, et al., *Chem., Int. Ed.* 2008; 47:2853; Madden et al., *Chem Commun* (Camb). 2009 Oct. 7; (37): 5588-5590; Lau et al., *Chem. Soc. Rev.,* 2015, 44:91-102; and Gunnoo et al., *Org. Biomol. Chem.,* 2016, 14:8002-8013; all of which are incorporated by reference herein in their entirety). The structurally stabilized peptides are designed to maintain the helix structure or other constrained structure. The peptide helix is an important mediator of key protein-protein interactions that regulate many important biological processes (e.g., apoptosis); however, when such a helix is taken out of its context within a protein and prepared in isolation, it usually adopts a random coil conformation, leading to a drastic reduction in biological activity and thus diminished therapeutic potential. In some cases, the structurally stabilized peptides comprise at least two modified amino acids joined by an internal (intramolecular) cross-link (or staple), and can maintain the helix structure.

In certain embodiments, polypeptides can be stabilized by peptide stapling (see, e.g., Walensky, *J. Med. Chem.,* 57:6275-6288 (2014), the contents of which are incorporated by reference herein in its entirety). A peptide is "stabilized" in that it maintains its native secondary structure. Stapling allows a polypeptide, predisposed to have an α-helical secondary structure, to maintain its native α-helical conformation. This secondary structure increases resistance of the polypeptide to proteolytic cleavage and heat, and also may increase target binding affinity, hydrophobicity, and cell permeability. Accordingly, the stapled (cross-linked) polypeptides described herein have improved biological activity relative to a corresponding non-stapled (uncross-linked) polypeptide.

The stabilized peptide can be a stapled peptide or multiply stapled peptide. The term "multiply stapled" polypeptides refers to those polypeptides containing more than one individual staple, and may contain two, three, or more independent staples of various spacing. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed, e.g., in WO 2008/121767 and WO 2010/068684, which are both hereby incorporated by reference in their entirety. In some instances, staples, as used herein, can retain the unsaturated bond or can be reduced.

In certain embodiments, polypeptides can be stabilized by, e.g., hydrocarbon stapling. In certain instances, the stapled peptide includes at least two (e.g., 2, 3, 4, 5, 6) amino acid substitutions, wherein the substituted amino acids are separated by two, three, or six amino acids, and wherein the substituted amino acids are non-natural amino acids with olefinic side chains. There are many known non-natural or unnatural amino acids any of which may be included in the stapled peptides. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and/or para-substituted phenylalanines (e.g., substituted with —C(=O)C$_6$H$_5$; —CF$_3$; —CN; -halo; —NO$_2$; CH$_3$), disubstituted phenylalanines, substituted tyrosines (e.g., further substituted with —C=O)C$_6$H$_5$; —CF$_3$; —CN; -halo; —NO$_2$; CH$_3$), and statine. Additionally, amino acids can be derivatized to include amino acid residues that are hydroxylated, phosphorylated, sulfonated, acylated, or glycosylated.

Hydrocarbon stapled polypeptides include one or more tethers (linkages) between two non-natural amino acids, which tether significantly enhances the α-helical secondary structure of, or constraint imposed on, the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, for example, where a peptide has the sequence . . . X1, X2, X3, X4, X5, X6, X7, X8, X9 . . . , cross-links between X1 and X4, or between X1 and X5, or between X1 and X8 are useful hydrocarbon stapled forms of that peptide, as are cross-links between X2 and X5, or between X2 and X6, or between X2 and X9, etc. The use of multiple cross-links (e.g., 2, 3, 4, or more) is also contemplated. The use of multiple cross-links is very effective at stabilizing and optimizing the peptide, especially with increasing peptide length. Thus, the disclosure encompasses the incorporation of more than one cross-link within the polypeptide sequence to either further stabilize the sequence or facilitate the structural stabilization, proteolytic resistance, acid stability, thermal stability, cellular permeability, and/or biological activity enhancement of longer polypeptide stretches. Additional description regarding making and use of hydrocarbon stapled polypeptides can be found, e.g., in U.S. Patent Publication Nos. 2012/0172285, 2010/0286057, and 2005/0250680, the contents of all of which are incorporated by reference herein in their entireties.

In certain embodiments when a staple is at the i and i+3 residues, R-propenylalanine and S-pentenylalanine; two R-pentenylalanines; or two S-pentenylalanines are substituted for the amino acids at those positions. In certain embodiments when a staple is at the i and i+4 residues, S-pentenyl alanine is substituted for the amino acids at those positions. In certain embodiments when a staple is at the i and i+7 residues, S-pentenyl alanine and R-octenyl alanine are substituted for the amino acids at those positions. In some instances, when the peptide is stitched, the amino acids of the peptide to be involved in the "stitch" are substituted with bis-pentenylglycine, S-pentenylalanine, and R-octenylalanine; or bis-pentenylglycine, S-octenylalanine, and R-octenylalanine.

Staple or stitch positions can be varied by testing different staple locations in a staple walk.

Figure 8A:
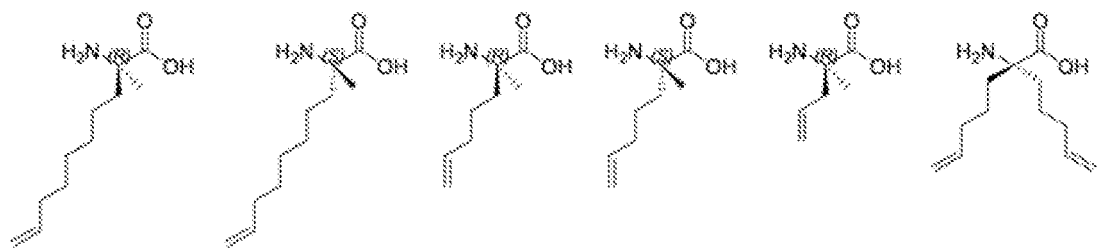
FIG. 8A shows the chemical structures of exemplary unnatural amino acids used to generate various kinds of staples.
Figure 8B:
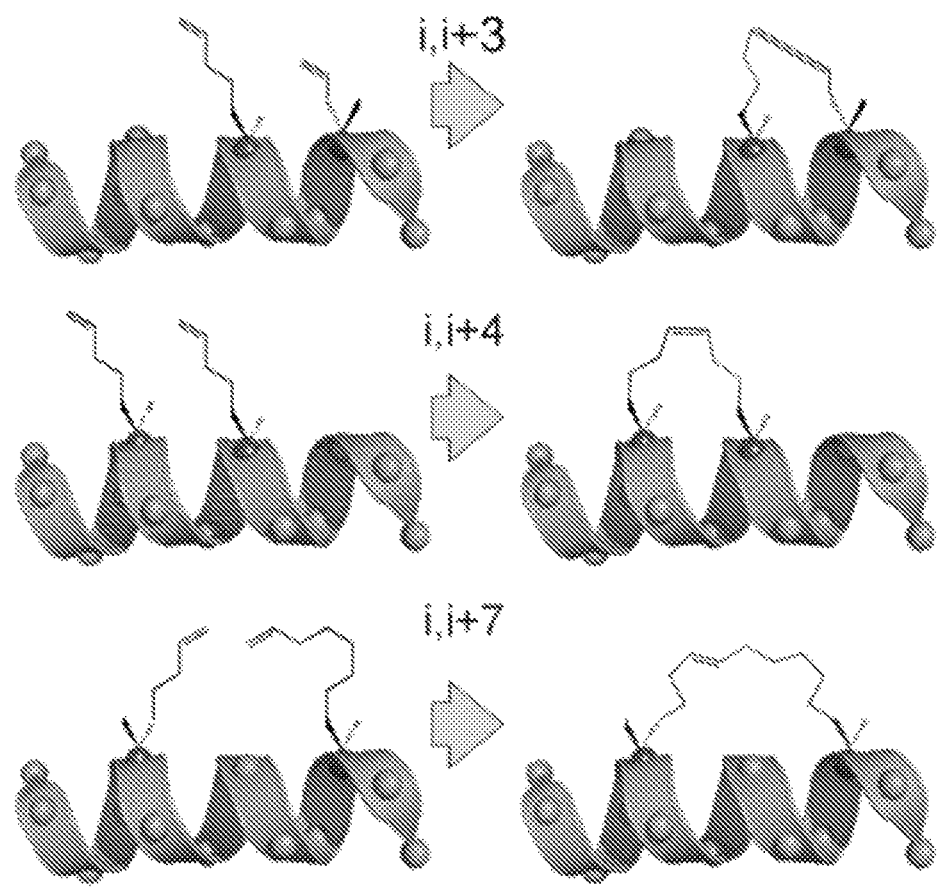
FIG. 8B illustrates peptides with staples of various lengths.
Figure 8C:
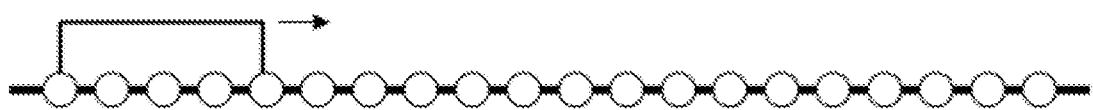
FIG. 8C illustrates a staple walk along a peptide sequence.
Figure 9:
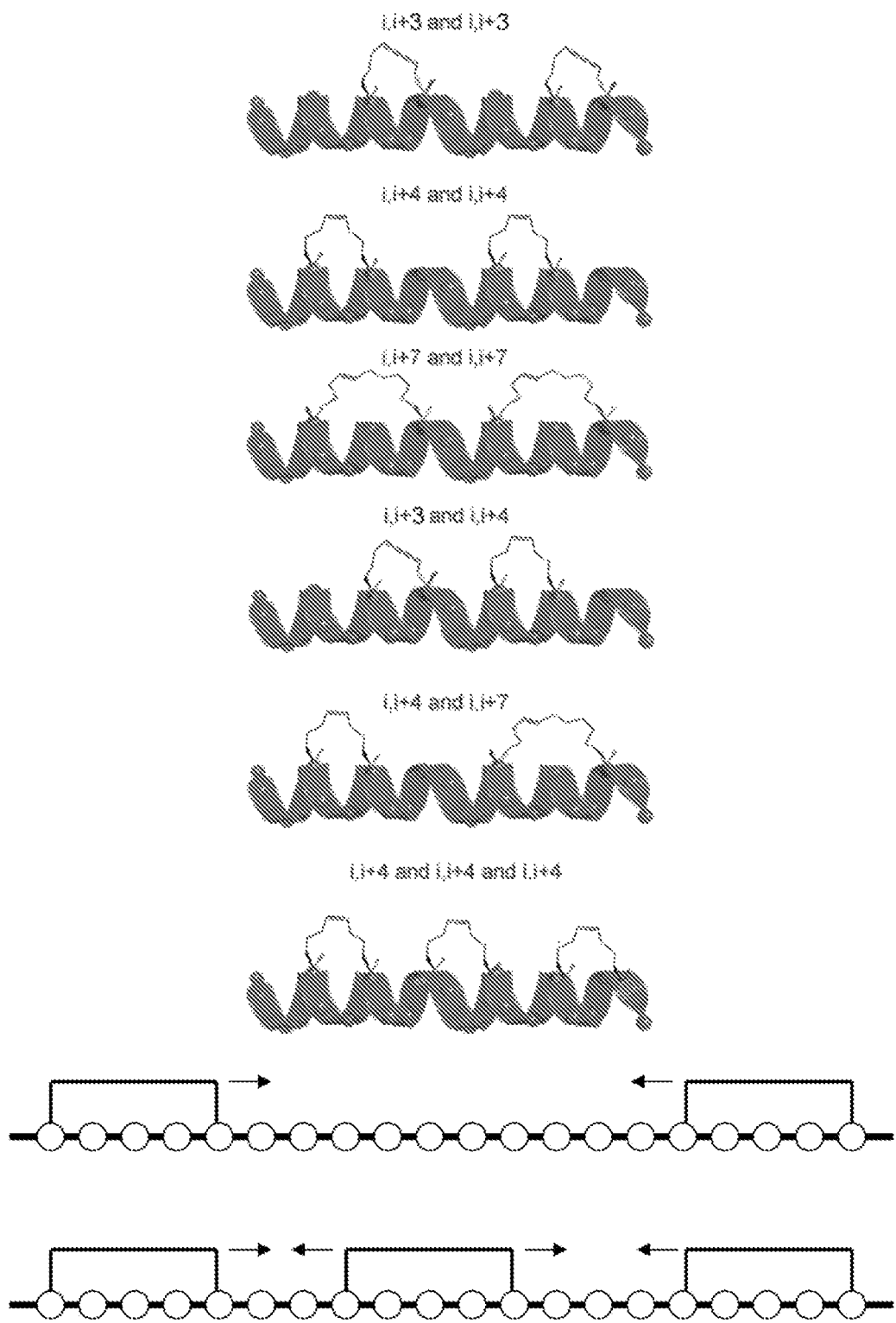
FIG. 9 is a schematic diagram showing representations of various kinds of double and triple stapling strategies along with exemplary staple walks.
Figure 10:
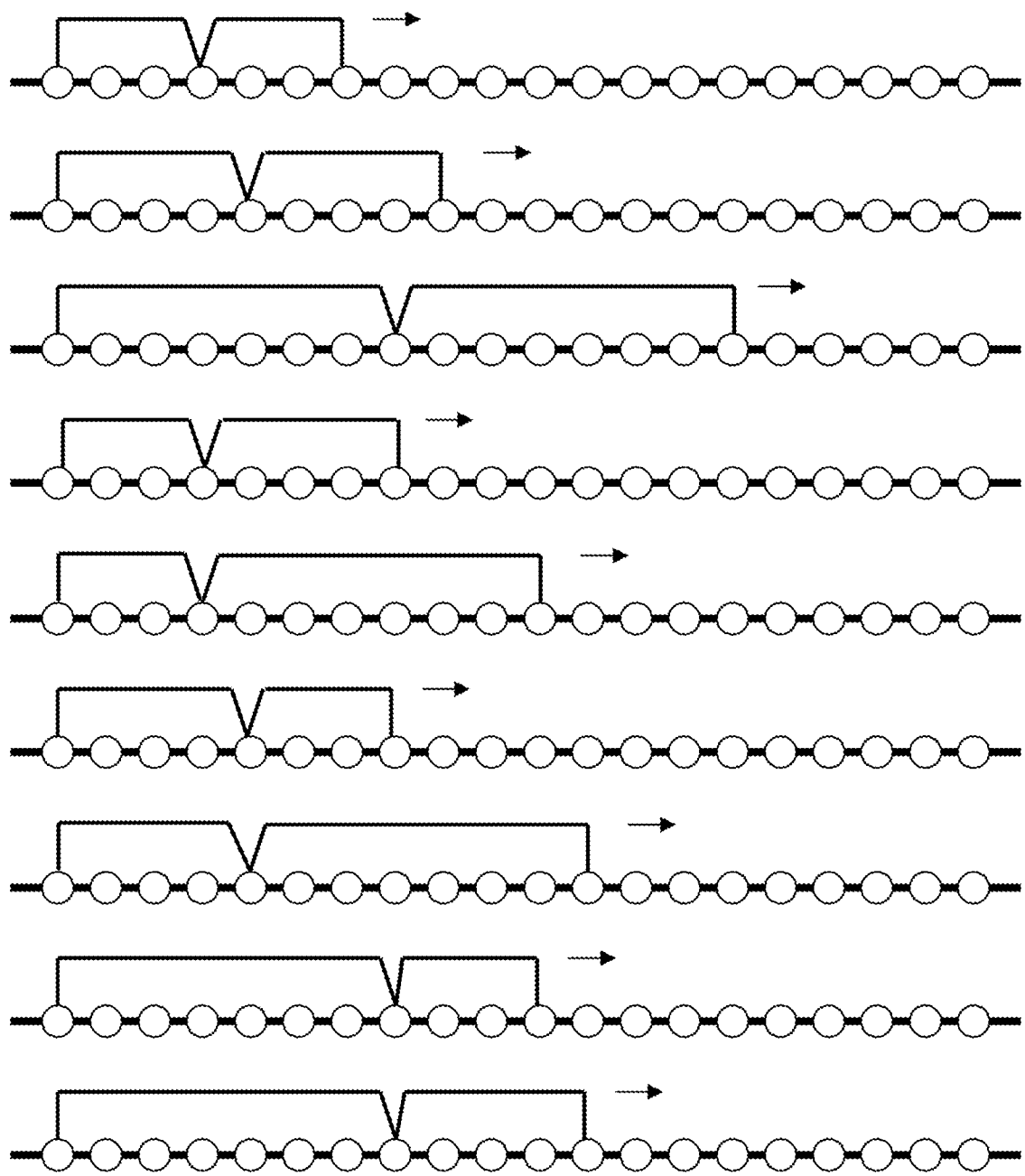
FIG. 10 is a schematic diagram showing exemplary staple walks using various lengths of branched double staple moieties.

FIG. 8A shows exemplary chemical structures of non-natural amino acids that can be used to generate various crosslinked compounds. FIG. 8B illustrates peptides with hydrocarbon cross-links between positions i and i+3; i and i+4; and i and i+7 residues. FIG. 8C illustrates a staple walk along a peptide sequence. FIG. 9 shows various peptide sequences with double and triple stapling strategies, and exemplary staple walks. FIG. 10 illustrates exemplary staple walks using various lengths of branched stitched moieties.

In one aspect, a stabilized polypeptide has the formula (I),

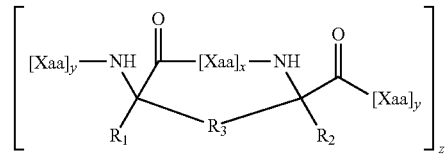

wherein:
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;
$R_3$ is alkyl, alkenyl, alkynyl; $[R_4—K—R_4]_n$; each of which is substituted with 0-6 $R_5$;
$R_4$ is alkyl, alkenyl, or alkynyl;
$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;
K O, S, SO, $SO_2$, CO, $CO_2$, $CONR_6$, or

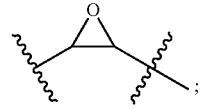

$R_6$ is H, alkyl, or a therapeutic agent;
n is an integer from 1-4;
x is an integer from 2-10;
each y is independently an integer from 0-100;
z is an integer from 1-10 (e.g., 1, 2, 3, 4, 5, 6, 7, 8, 9, 10);
and each Xaa is independently an amino acid.

The tether can include an alkyl, alkenyl, or alkynyl moiety (e.g., $C_5$, $C_8$, or $C_{11}$ alkyl, a $C_5$, $C_8$, or $C_{11}$ alkenyl, or $C_5$, $C_8$, or $C_{11}$ alkynyl). The tethered amino acid can be alpha disubstituted (e.g., $C_1$-$C_3$ or methyl).

In some instances, x is 2, 3, or 6. In some instances, each y is independently an integer between 1 and 15, or 3 and 15. In some instances, $R_1$ and $R_2$ are each independently H or $C_1$-$C_6$ alkyl. In some instances, $R_1$ and $R_2$ are each independently $C_1$-$C_3$ alkyl. In some instances, at least one of $R_1$ and $R_2$ are methyl. For example, $R_1$ and $R_2$ can both be methyl. In some instances, $R_3$ is alkyl (e.g., $C_8$ alkyl) and x is 3. In some instances, $R_3$ is $C_{11}$ alkyl and x is 6. In some instances, $R_3$ is alkenyl (e.g., $C_8$ alkenyl) and x is 3. In some instances, x is 6 and $R_3$ is C11 alkenyl. In some instances, $R_3$ is a straight chain alkyl, alkenyl, or alkynyl. In some instances, $R_3$ is —CH$_2$—CH$_2$—CH$_2$—CH=CH—CH$_2$—CH$_2$—CH$_2$—.

In another aspect, the two alpha, alpha disubstituted stereocenters are both in the R configuration or S configuration (e.g., i, i+4 cross-link), or one stereocenter is R and the other is S (e.g., i, i+7 cross-link). Thus, where formula I is depicted as:

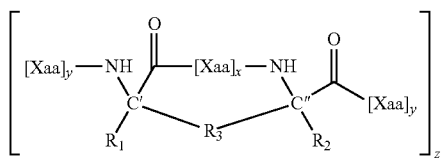

the C' and C" disubstituted stereocenters can both be in the R configuration or they can both be in the S configuration, e.g., when x is 3. When x is 6, the C' disubstituted stereocenter is in the R configuration and the C" disubstituted stereocenter is in the S configuration. The $R_3$ double bond can be in the E or Z stereochemical configuration.

In some instances, $R_3$ is $[R_4-K-R_4]_n$; and $R_4$ is a straight chain alkyl, alkenyl, or alkynyl.

In some embodiments, the disclosure provides internally cross-linked ("stapled" or "stitched") peptides, wherein the side chains of two amino acids separated by two, three, or six amino acids are replaced by an internal staple; the side chains of three amino acids are replaced by an internal stitch; the side chains of four amino acids are replaced by two internal staples, or the side chains of five amino acids are replaced by the combination of an internal staple and an internal stitch. The stapled/stitched peptide can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length.

In some embodiments, the stabilized peptide is a peptide of an intracellular protein. In some embodiments, the stabilized peptide is a peptide of a disease causing or disease-related protein. In some embodiments, the stabilized peptide is a peptide of a bacterial protein. In some embodiments, the stabilized peptide is a peptide of a human protein. In some embodiments, the stabilized peptide is a peptide of an oncogenic protein. Non-limiting examples of oncogenic proteins include BCL-2, $BCLX_L$, MCL-1, BFL-1, BCL-w, BCL-B, EZH2, HDM2/HDMX, KRAS/NRAS/HRAS, MYC, β-catenin, PI3K, PTEN, TSC, AKT, BRCA1/2, a EWS-FLI fusion, an MLL fusion, a receptor tyrosine kinase, a HOX homolog, JUN, Cyclin D, Cyclin E, BRAF, CRAF, CDK4, CDK2, HPV-E6/E7, Aurora kinase, MITF, Wnt1, PD-1, BCR, and CCR5.

Non-limiting examples of stapled peptides are listed below:

```
PUMA
                                        (SEQ ID NO: 46)
QWAREIGAQLRX₁BADX₂LNAQYERR

EZH2
                                        (SEQ ID NO:47)
FSSNRX₁KILX₂RTQILNQEWKQRRIQPV

SOS
                                        (SEQ ID NO: 48)
RRFFGIX₁LTNX₂LKTEEGN

MCL-1
                                        (SEQ ID NO: 49)
RKALETLRRVGDGVX₁RNHX₂TAF

BCL9
                                        (SEQ ID NO: 50)
LSQEQLEHRERSLX₁TLRX₂IQRBLF p53
                                        (SEQ ID NO: 51)
LTF8EYWAQ#XSAA

BID
                                        (SEQ ID NO: 52)
DIIRNIARHLAX₁VGDX₂BDRSI

BIM
                                        (SEQ ID NO: 53)
IWIAQELRX₁IGDX₂FNAYYARR

BAD S153D
                                        (SEQ ID NO: 54)
NLWAAQRYGRELRX₁BDDX₂FVDSFKK

BAD
                                        (SEQ ID NO: 55)
NLWAAQRYGRELRX₁BSDX₂FVDSFKK

HRK
                                        (SEQ ID NO: 56)
QLTAARLKX₁LGDX₂LHQRTBWR

NOXA
                                        (SEQ ID NO: 57)
AELEVESATQLRX₁FGDX₂LNFRQKLL
``` wherein, 8=R-octenyl alanine; B=norleucine; #=cyclobutylalanine; X=pentenyl alanine (e.g., (S)-2-(4'-pentenyl)alanine), or any other non-natural amino acid, or any agent that permits stapling, and, in some instances, $X_1$ and $X_2$ are the same (e.g., S-pentenyl alanine or (S)-2-(4'-pentenyl)alanine).

In some embodiments, the stapled polypeptide comprises or consists of the amino acid sequence set forth in any one of SEQ ID NOs: 46 to 57. In some embodiments, this disclosure features stabilized peptides that differ from the peptides disclosed above in that they vary in the location of the staple/stitch. In certain embodiments, this disclosure features stabilized peptides that differ from the peptides disclosed above in that they vary from the above-disclosed sequences in having 1 to 7 (e.g., 1, 2, 3, 4, 5, 6, 7) amino acid substitutions on the non-interacting face of the alpha-helix of these peptides. In certain instances, the substitutions are conservative. In other instances, the substitutions are non-conservative. In certain embodiments, this disclosure features stabilized peptides that differ from the peptides disclosed above in that they vary from the above-disclosed sequences in having 1 to 5 (e.g., 1, 2, 3, 4, 5) amino acid substitutions on the interacting face of the alpha-helix of these peptides. In certain instances, the substitutions are conservative.

In certain embodiments, the stapled peptide is a BCL-2 homology 3 (BH3) domain polypeptide (e.g., a BH3 domain from MCL-1, an MCL-1 Stabilized Alpha Helix of BCL-2 domain (SAHB), or MCL-1 $SAHB_D$).

Non-limiting examples of other stabilized peptides that can be employed in the methods described herein are provided in U.S. Pat. Nos. 9,834,581; 9,822,165; 9,695,224; 9,617,309; 9,579,395; 9,556,229; 9,556,227; 9,527,896; 9,522,947; 9,517,252; 9,505,816; 9,505,804; 9,505,801; 9,493,510; 9,464,125; 9,485,202; 9,458,189; 9,416,162; 9,408,885; 9,346,868; 9,296,805; 9,227,995; 9,175,047; 9,175,045; 9,163,330; 9,096,684; 9,079,970; 8,957,026; 8,937,154; 8,933,109; 8,927,500; 8,889,632; 8,592,377; 8,586,707; 8,324,153; and U.S. Patent Application Publication Nos. 20170247423; 20170240604; 20170212125; 20170165320; 20170066747; 20170015716; 20160376336; and 20160244494, the contents of all of which are incorporated by reference in their entirety herein (especially the disclosure of stabilized (e.g., stapled or stitched) peptides).

While hydrocarbon tethers are common, other tethers can also be employed in the stabilized peptides (in one or both of the cell permeable stapled peptide and the cargo) described herein. For example, the tether can include one or more of an ether, thioether, ester, amine, or amide, or triazole moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid. Triazole-containing (e.g., 1,4 triazole or 1,5 triazole) crosslinks can be used (see, e.g., Kawamoto et al. 2012 *Journal of Medicinal Chemistry* 55:1137; WO 2010/060112). In addition, other methods of performing different types of stapling are well known in the art and can be employed (see, e.g., *Lactam stapling*: Shepherd et al., *J. Am. Chem. Soc.*, 127:2974-2983 (2005); *UV-cycloaddition stapling*: Madden et al., *Bioorg. Med. Chem. Lett.*, 21:1472-1475 (2011); *Disulfide stapling*: Jackson et al., *Am. Chem. Soc.*, 113:9391-9392 (1991); *Oxime stapling*: Haney et al., *Chem. Commun.*, 47:10915-10917 (2011); *Thioether stapling*: Brunel and Dawson, *Chem. Commun.*, 552-2554 (2005); *Photoswitchable stapling*: J. R. Kumita et al., *Proc. Natl. Acad. Sci. U.S.A.*, 97:3803-3808 (2000); *Double-click stapling*: Lau et al., *Chem. Sci.*, 5:1804-1809 (2014); *Bis-lactam stapling*: J. C. Phelan et al., *J. Am. Chem. Soc.*, 119:455-460 (1997); and *Bis-acylation stapling*: A. M. Spokoyny et al., *J. Am. Chem. Soc.*, 135:5946-5949 (2013)).

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while tethers spanning from amino acids i to i+3, i to i+4, and i to i+7 are common in order to provide a tether that is primarily on a single face of the alpha helix, the tethers can be synthesized to span any combinations of numbers of amino acids and also used in combination to install multiple tethers.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation, aminohydroxylation or dihydroxylation) to provide one of compounds below.

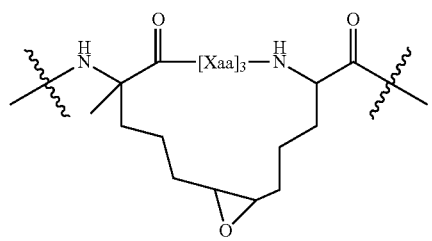

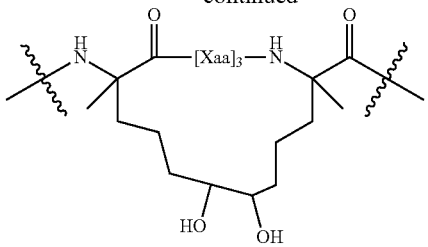

Either the epoxide moiety or one of the free hydroxyl moieties can be further functionalized. For example, the epoxide can be treated with a nucleophile, which provides additional functionality that can be used, for example, to attach a therapeutic agent. Such derivatization can alternatively be achieved by synthetic manipulation of the amino or carboxy-terminus of the polypeptide or via the amino acid side chain. Other agents can be attached to the functionalized tether, e.g., an agent that facilitates entry of the polypeptide into cells.

In some embodiments, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The stapled polypeptides can include a drug, a toxin, a derivative of polyethylene glycol; a second polypeptide; a carbohydrate, etc. Where a polymer or other agent that is linked to the stapled polypeptide can be desirable for the composition to be substantially homogeneous.

The addition of polyethylene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

$XO-(CH_2CH_2O)_n-CH_2CH_2-Y$ where n is 2 to 10,000 and X is H or a terminal modification, e.g., a $C_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. The intermediate linker can be any linker known in the art. In some embodiments, the linker can comprise naturally occurring amino acids, non-naturally occurring amino acids (e.g., beta-alanine amino acids), or a combination thereof. In some embodiments, the linker can comprise, consist of, or consist essentially of beta-alanine amino acids. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as —NH(CH$_2$)$_n$C(O)—, wherein n=2-20 can be used. These alkyl linkers may further be substituted by any non-sterically hindering group such as lower alkyl (e.g., C$_1$-C$_6$) lower acyl, halogen (e.g., Cl, Br), CN, NH$_2$, phenyl, etc. U.S. Pat. No. 5,446,090 describes a bifunctional PEG linker and its use in forming conjugates having a peptide at each of the PEG linker termini.

The stabilized peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration.

Synthesizing the Stabilized Peptides

Methods of synthesizing the stabilized peptides described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The stabilized peptides can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-NH$_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides can be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide as described herein, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond (NH—CH$_2$); a thiomethylene bond (S—CH$_2$ or CH$_2$—S); an oxomethylene bond (O—CH$_2$ or CH$_2$—O); an ethylene bond (CH$_2$—CH$_2$); a thioamide bond (C(S)—NH); a trans-olefin bond (CH=CH); a fluoro substituted trans-olefin bond (CF=CH); a ketomethylene bond (C(O)—CHR) or CHR—C(O) wherein R is H or CH$_3$; and a fluoro-ketomethylene bond (C(O)—CFR or CFR—C(O) wherein R is H or F or CH$_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof.

α, α-Disubstituted non-natural amino acids containing olefinic side chains of varying length can be synthesized by known methods (Williams et al. *J. Am. Chem. Soc.*, 113: 9276, 1991; Schafmeister et al., *J. Am. Chem Soc.*, 122: 5891, 2000; and Bird et al., *Methods Enzymol.*, 446:369, 2008; Bird et al, *Current Protocols in Chemical Biology*, 2011). For peptides where an i linked to i+7 staple is used (two turns of the helix stabilized) either: a) one S5 amino acid and one R8 is used; or b) one S8 amino acid and one R5 amino acid is used. R8 is synthesized using the same route, except that the starting chiral auxiliary confers the R-alkyl-stereoisomer. Also, 8-iodooctene is used in place of 5-iodopentene. Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-S$_5$—OH, Fmoc-R$_8$—OH, Fmoc-R$_8$—OH, Fmoc-S$_8$—OH and Fmoc-R$_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, CA). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., *Org. Synth.*, 80:31, 2003).

Again, methods suitable for obtaining (e.g., synthesizing), stapling, and purifying the peptides disclosed herein are also known in the art (see, e.g., Bird et. al., *Methods in Enzymol.*, 446:369-386 (2008); Bird et al, *Current Protocols in Chemical Biology*, 2011; Walensky et al., *Science*, 305:1466-1470 (2004); Schafmeister et al., *J. Am. Chem. Soc.*, 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety).

In some embodiments, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Properties of the stabilized (e.g., stapled) polypeptides described herein can be assayed, for example, using the methods described below.

Assays to Determine α-Helicity: Compounds are dissolved in an aqueous solution (e.g. 5 mM potassium phosphate solution at pH 7, or distilled $H_2O$, to concentrations of 25-50 μM). Circular dichroism (CD) spectra are obtained on a spectropolarimeter (e.g., Jasco J-710, Aviv) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity by the reported value for a model helical decapeptide (Yang et al., *Methods Enzymol.* 130:208 (1986)).

Assays to Determine Melting Temperature (Tm): Crosslinked or the unmodified template peptides are dissolved in distilled $H_2O$ or other buffer or solvent (e.g. at a final concentration of 50 μM) and Tm is determined by measuring the change in ellipticity over a temperature range (e.g. 4 to 95° C.) on a spectropolarimeter (e.g., Jasco J-710, Aviv) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

In Vitro Protease Resistance Assays: The amide bond of the peptide backbone is susceptible to hydrolysis by proteases, thereby rendering peptidic compounds vulnerable to rapid degradation in vivo. Peptide helix formation, however, typically buries and/or twists and/or shields the amide backbone and therefore may prevent or substantially retard proteolytic cleavage. The peptidomimetic macrocycles may be subjected to in vitro enzymatic proteolysis (e.g. trypsin, chymotrypsin, pepsin) to assess for any change in degradation rate compared to a corresponding uncrosslinked or alternatively stapled polypeptide. For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 mcg) are incubated with trypsin agarose (Pierce) (S/E~125) for 0, 10, 20, 90, and 180 minutes. Reactions are quenched by tabletop centrifugation at high speed; remaining substrate in the isolated supernatant is quantified by HPLC-based peak detection at 280 nm. The proteolytic reaction displays first order kinetics and the rate constant, k, is determined from a plot of ln[S] versus time.

Peptidomimetic macrocycles and/or a corresponding uncrosslinked polypeptide can be each incubated with fresh mouse, rat and/or human serum (e.g. 1-2 mL) at 37° C. for, e.g., 0, 1, 2, 4, 8, and 24 hours. Samples of differing macrocycle concentration may be prepared by serial dilution with serum. To determine the level of intact compound, the following procedure may be used: The samples are extracted, for example, by transferring 100 μL of sera to 2 ml centrifuge tubes followed by the addition of 10 μL of 50% formic acid and 500 μL acetonitrile and centrifugation at 14,000 RPM for 10 min at 4+/−2° C. The supernatants are then transferred to fresh 2 ml tubes and evaporated on Turbovap under $N_2$<10 psi, 37° C. The samples are reconstituted in 100 μL of 50:50 acetonitrile:water and submitted to LC-MS/MS analysis. Equivalent or similar procedures for testing ex vivo stability are known and may be used to determine stability of macrocycles in serum.

In Vivo Protease Resistance Assays: A key benefit of peptide stapling is the translation of in vitro protease resistance into markedly improved pharmacokinetics in vivo.

In vitro Binding Assays: To assess the binding and affinity of peptidomimetic macrocycles and peptidomimetic precursors to acceptor proteins, a fluorescence polarization assay (FPA) can be used, for example. The FPA technique measures the molecular orientation and mobility using polarized light and fluorescent tracer. When excited with polarized light, fluorescent tracers (e.g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution).

In Vitro Cell Uptake Assays: To assess cellular uptake of cargoes that are bound to cell-permeable stapled peptide modules, fluorescent tracers (e.g. TAMRA, FITC) are attached to the cell-permeable stapled peptide modules or the cargos. The cellular uptake can be tracked by, e.g., epifluorescence microscopy, fluorescence microscopy, confocal microscopy, and/or flow cytometry, at different time periods. In this manner, the rate of uptake and the intracellular distribution patterns of the stabilized peptides (e.g., CPSPs and CPSP-conjugates, other cell-permeable stapled peptides) can also be determined.

Intracellular binding Assays: To assess the binding of the CPSP-fusions to their respective protein target(s), cells were transfected with a GFP binding nanobody fraction coupled to nuclear lamina binding sequence (lamin B1). This nanobody binds to GFP tagged proteins and recruits them to the nuclear lamina allowing the recruitment and visualization of proteins interacting with the GFP tagged protein of interest. For example, GFP-MCL-1 can be expressed and localized to the nuclear lamina, followed by treatment of cells with TAMRA-labeled ATSP-7041/MCL-1 $SAHB_D$ fusion, followed by confocal microscopy imaging to monitor for the colocalization of TAMRA-labeled CPSP fusion at the nuclear lamina.

Methods of Use

The disclosure provides methods of delivering various cargos (e.g., various therapeutic agents or diagnostic agents) to a desired intracellular site. The methods involve contacting the cell with a compound comprising (1) the agent and (2) the cell-permeable stapled peptide described herein, wherein the agent is linked to the cell-permeable stapled peptide.

The methods as described herein can also be used for the prophylaxis and/or treatment of various diseases, e.g., a cancer, a neurodegenerative disease, an autoimmune disease, or an inflammatory disease. The terms "treat" or "treating," as used herein, refers to alleviating, inhibiting, or ameliorating the disease or condition from which the subject is suffering. In general, methods include selecting a subject and administering to the subject an effective amount of one or more of the compounds as described herein, e.g., in or as a pharmaceutical composition, and optionally repeating administration as required for the prophylaxis or treatment of a disease (e.g., cancer or an autoimmune disease), and can be administered orally, intravenously or topically.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments. For example, effective amounts can be administered at least once.

The disclosure also provides methods of delivering various cargos (e.g., various testing agents, diagnostic agent, or imaging agents) to the cell for various research and diagnostic purposes. The methods involve contacting the cell with a compound comprising (1) the agent and (2) the cell-permeable stapled peptide described herein, wherein the agent is linked to the cell-permeable stapled peptide. The agent (e.g., testing agent, therapeutic agent, diagnostic agent, or imaging agent) can be any agent that, when administered to a cell, has a therapeutic and/or diagnostic effect and/or elicits a desired biological and/or pharmacological effect. Therapeutic agents can include small molecules (both synthetic and natural), peptides, proteins (including antigen binding molecules), nucleic acids (plasmids, RNA interference agents, antisense agents), chemotherapeutic agents, radioactive agents, lipid-based agents, carbohydrate-based agents, and the like. The imaging agent or diagnostic agent can be any agent that is useful for imaging purposes or diagnostic purposes. Example of diagnostic agents or imaging agents include, e.g., a fluorescent molecule, a radioactive molecule (e.g., comprising a radioisotope), a contrast agent, a lithographic agent, an agent sensitive to ultraviolet light, or an agent sensitive to visible light. Cargos comprising an imaging agent can be used, e.g., to identify the location, size or other information of the cells (e.g., tumor cells). Such information can be used in methods for diagnosis and/or treatment, e.g., to direct surgeries for removal of targeted cells, tissues or organs. The cell can be any cells known in the art, including e.g., bacteria, and eukaryotic cell. Eukaryotic cells include e.g., animal cells (e.g., mammalian cells, human cells, or murine cells), plant cells, and yeast. The term also includes cells from cell lines, e.g., mammalian cell lines such as HeLa cells, as well as embryonic cells, e.g., embryonic stem cells and collections of cells in the form of, e.g., a tissue. Various cell types can also be used in the methods of the present disclosure, including, e.g., differentiated cells, such as epithelial cells, cardio myocytes, neural cells, epidermal cells, keratinocytes, hematopoietic cells, melanocytes, chondrocytes, B-cells, T-cells, erythrocytes, macrophages, monocytes, fibroblasts, lymphocytes, or muscle cells; and undifferentiated cells, such as embryonic, mesenchymal, or adult stem cells. Additional cell types that can be used by the methods of the disclosure include gametocytes, oocytes, sperm, zygotes, and embryos. Other cells include those from the bladder, brain, esophagus, fallopian tube, heart, intestines, gallbladder, kidney, liver, lung, ovaries, pancreas, prostate, spinal cord, spleen, stomach, testes, thymus, thyroid, trachea, ureter, urethra, or uterus.

Pharmaceutical Compositions

One or more of any of the compounds (e.g., cell permeable stapled peptides coupled with cargos) described herein can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intraarterial, subdermally, intraperitoneally, intramuscularly, and/or subcutaneously); and/or for oral administration, transmucosal administration, and/or topical administration (including topical (e.g., nasal) sprays and/or solutions).

In some embodiments, pharmaceutical compositions can include an effective amount of one or more stabilized peptides (e.g., cell-permeable stapled peptide with cargos). The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of infection).

Pharmaceutical compositions described herein can include one or more peptides and any pharmaceutically acceptable carrier and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a compound as described herein, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions can include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions as described herein may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

EXAMPLES

The invention is further described in the following examples, which do not limit the scope of the invention described in the claims.

Example 1: Construction of Cell-Permeable Stapled Peptide Modules

A series of cell-permeable stapled peptides (CPSP) applied as modules for efficient entry and transport of cargoes into living cells were synthesized. These peptides can target the cytoplasm and/or discrete subcellular organelles or structures such as the nucleus, the nucleolus, and the mitochondria.

The sequence motif for these peptides comprises the sequence $X_1R_2R_3R_4X_5$ (SEQ ID NO: 10), wherein $R_2$, $R_3$, and $R_4$ are arginine, in either the L form or the D form, and $X_1$ and $X_5$ are non-natural amino acids, e.g., (S)-2-(4'-pentenyl) alanine. As shown in Table 2, TAMRA labeled CPSP 1-9 were synthesized. In addition, L-CPSP, which consists of CPSP3 coupled to a cargo (B G V A D L I K K F E X I A K X E K (SEQ ID NO: 23), wherein X is (S)-2-(4'-pentenyl)alanine) by a G5 linker (GGGGG; SEQ ID NO: 28), was also synthesized.

Synthesis of these peptides was performed using Fmoc solid-phase synthesis and ruthenium-catalyzed olefin metathesis, followed by peptide deprotection and cleavage, purification by reverse phase high performance liquid chromatography/mass spectrometry (LC/MS), and quantification by amino acid analysis. A detailed description regarding the methods of synthesis can be found e.g., in Bird et al. "Synthesis and Biophysical Characterization of Stabilized α-Helices of BCL-2 Domains." *Methods in Enzymology*, 446 (2008): 369-386.

TABLE 2

| Name | Sequence |
| --- | --- |
| TAMRA-CPSP1 | * Ba X R r R X R (SEQ ID NO: 12) |
| TAMRA-CPSP2 | * Ba X R r R X (SEQ ID NO: 13) |
| TAMRA-CPSP3 | * Ba X R r R X R B (SEQ ID NO: 14) |
| TAMRA-CPSP4 | * Ba X R r R X B (SEQ ID NO: 15) |
| TAMRA-CPSP5 | * Ba X R r R X R Naph (SEQ ID NO: 16) |
| TAMRA-CPSP6 | * Ba X R r R X Naph (SEQ ID NO: 17) |
| TAMRA-CPSP7 | * Ba X R R R X R B (SEQ ID NO: 18) |
| TAMRA-CPSP8 | * Ba X R r R X R B G B R X R r R X (SEQ ID NO: 19) |
| TAMRA-CPSP9 | * Ba X R r R X R B G X R r R X R B (SEQ ID NO: 20) |
| TAMRA-L-CPSP3 | Ac B G V A D L I K K F E X I A K X E K* G G G G G X R r R X R B (SEQ ID NO: 21) |
| TAMRA-MCL-1 SAHB$_D$/ATSP-7041 | * Ba R K A L E T L R R V B D G V X R N H X T A F G G G G G L T F 8 E Y W A Q CycB X S A A (SEQ ID NO: 22) |
| TAMRA-ATSP-7041/PNA | * Ba LTF8EYWAQ CycB XSAAAGGGGGK (SEQ ID NO: 61) -[GCCTAGTTTATCACCAATAAT] (SEQ ID NO: 62) |

TABLE 2-continued

| Name | Sequence |
|---|---|
| TAMRA-CPSP3/vMIA | * Ba XRrRXRB-GZG-EALKKALRRHRFLWQR RQRA (SEQ ID NO: 63) |

*: 5-(and-6)-Carboxytetramethylrhodamine (TAMRA)
K*: TAMRA conjugated to primary amine of K
Ba: beta-alanine
X: (S)-2-(4'-pentenyl)alanine
Naph: 2-naphthyl-L-alanine
r: D-Arginine
R: L-Arginine
B: Norleucine
CycB: cyclobutylalanine
8: R-octenyl alanine
Ac: Acetyl group
[ ]: Nucleic acid sequence

Example 2: Cell-Permeable Stapled Peptide Carriers for Intracellular Cargo Delivery CPSP1-CPSP9 and L-CPSP (where L is an F-actin staining peptide) were labeled with a fluorescent dye, TAMRA. The sequences of these peptides are shown in Table 2 (SEQ ID NOs: 12-17 and 21). These TAMRA-labeled peptides (10 µM) were added to cell culture. After incubating the peptides with the cells for approximately 1 hour, the cells were examined by a fluorescence microscope. As shown in FIG. 1, TAMRA-labelled stapled peptides demonstrated robust intracellular labeling of treated cells. The distribution of these TAMRA-labelled stapled peptides are summarized in the table below.

TABLE 3

| Name | Distribution/Observations |
|---|---|
| TAMRA-CPSP1 | Cytosol; Nucleus; Nucleolus; Endosomes; lysosomes |
| TAMRA-CPSP2 | Cytosol; Nucleus; Nucleolus; Endosomes; lysosomes |
| TAMRA-CPSP3 | CPSP3 were enriched at mitochondria as well as Cytosol; Nucleus; Nucleolus; Endosomes; lysosomes |
| TAMRA-CPSP4 | Cytosol; Nucleus; Nucleolus; Endosomes; lysosomes |
| TAMRA-CPSP5 | Cytosol; Nucleus; Nucleolus; Endosomes; lysosomes |
| TAMRA-CPSP6 | Cytosol; Nucleus; Nucleolus; Endosomes; lysosomes |
| TAMRA-CPSP7 | Cytosol; Nucleus; Nucleolus; Endosomes; lysosomes |
| TAMRA-CPSP8 | Cytosol; Nucleus; Nucleolus; Endosomes; lysosomes |
| TAMRA-CPSP9 | Cytosol; Nucleus; Nucleolus; Endosomes; lysosomes |
| TAMRA-L-CPSP3 | Cytosol; Nucleus; Nucleolus; Endosomes; lysosomes; Actin filaments |

Figure 2:
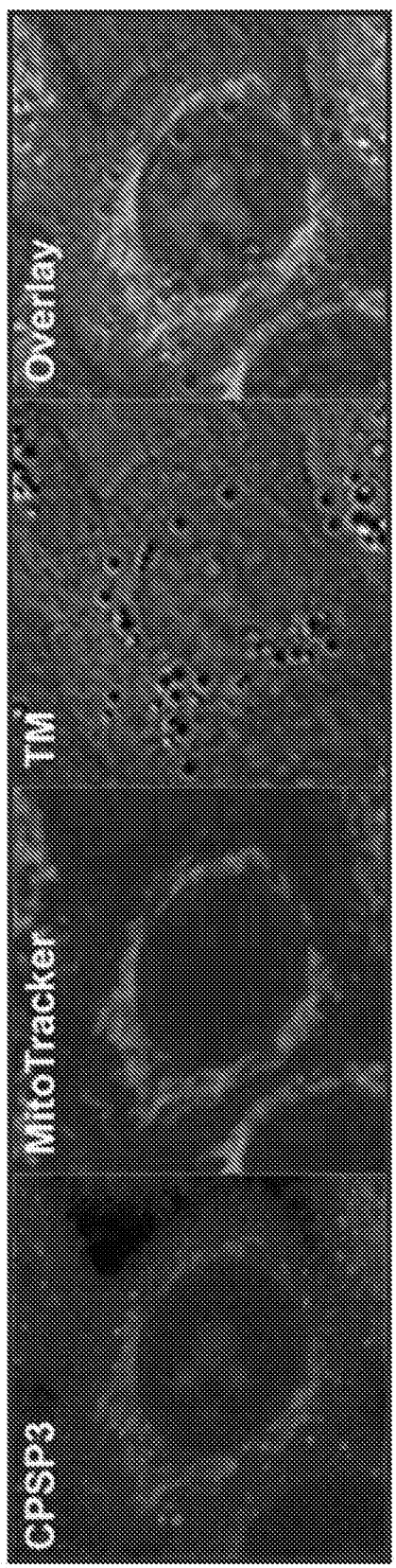
FIG. 2. Enrichment of TAMRA-labeled CPSP3 at the mitochondria.
Figure 3A:
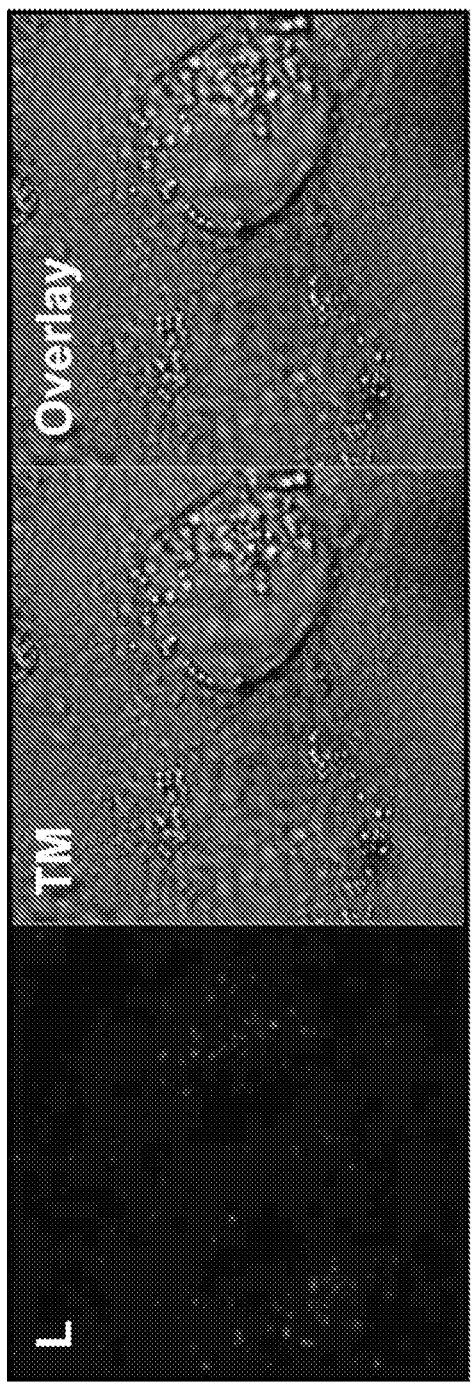
FIGS. 3A-3B. Transport of a cell impermeable F-actin staining peptide into the cell upon fusion with CPSP3.
Figure 3B:
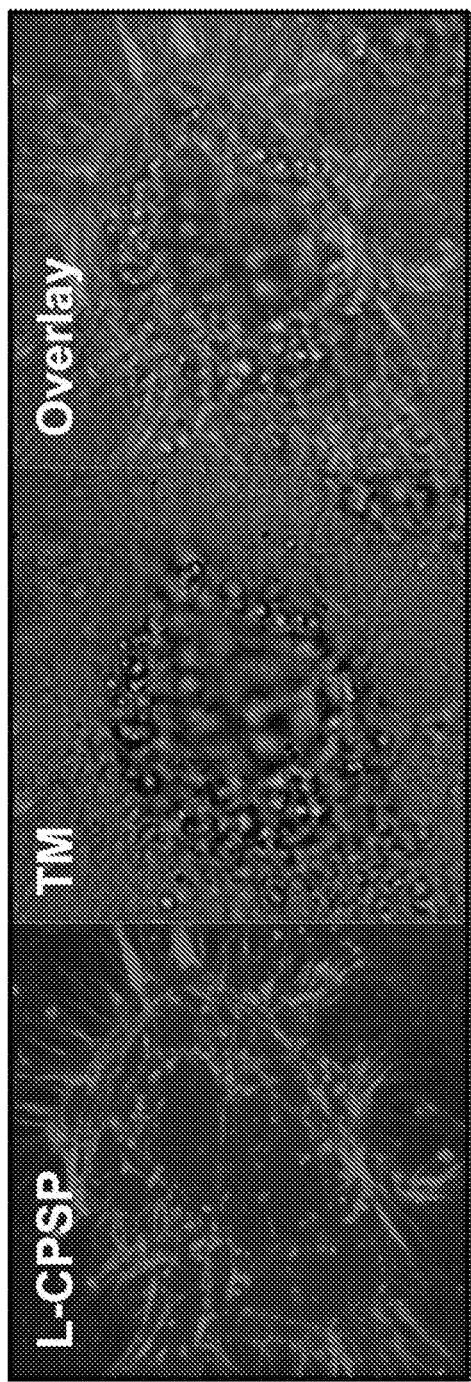

Furthermore, TAMRA-labeled CPSP3 (SEQ ID NO: 14) (10 µM) and MitoTracker were both added to the cell culture. As shown in FIG. 2, co-labeling of CPSP3 with MitoTracker demonstrated enrichment of CPSP3 at the mitochondria of the treated cells. Whereas the F-actin staining peptide (L; 40 µM) is unable to enter intact cells on its own (FIG. 3A), conjugation to CPSP3 enables robust delivery of the peptide into the cell (TAMRA-L-CPSP3; 10 µM), with notable localization of L-CPSP3 to actin filaments (FIG. 3B). Strikingly, the fusion of CPSP3 to the F-actin binding peptide alters the distribution seen for CPSP3 alone (see FIGS. 2, 3B and Table 2).

Example 3: Chimeric CPSPs for Delivery of Prototype Therapies with Dual Functionalities A cell-permeable stapled peptide drug prototype, ATSP-7041 [LTF8EYWAQ CycB XSAA, wherein "8" is R-octenyl alanine, "CycB" is cyclobutylalanine, and "X" is (S)-2-(4'-pentenyl)alanine (SEQ ID NO: 11) was fused to a second stapled peptide construct with more limited cellular penetrance MCL-1 SAHB$_D$ (SEQ ID NO: 24). This polypeptide was further labeled with TAMRA, creating a chimeric construct (SEQ ID NO: 22) for intracellular delivery of two therapeutic functionalities. The sequence for SAHB$_D$ is shown below:

MCL-1 SAHB$_D$:
(SEQ ID NO: 24)
R K A L E T L R R V B D G V X R N H X T A F,
wherein X = (S)-2-(4'-pentenyl)alanine.

Figure 4A:
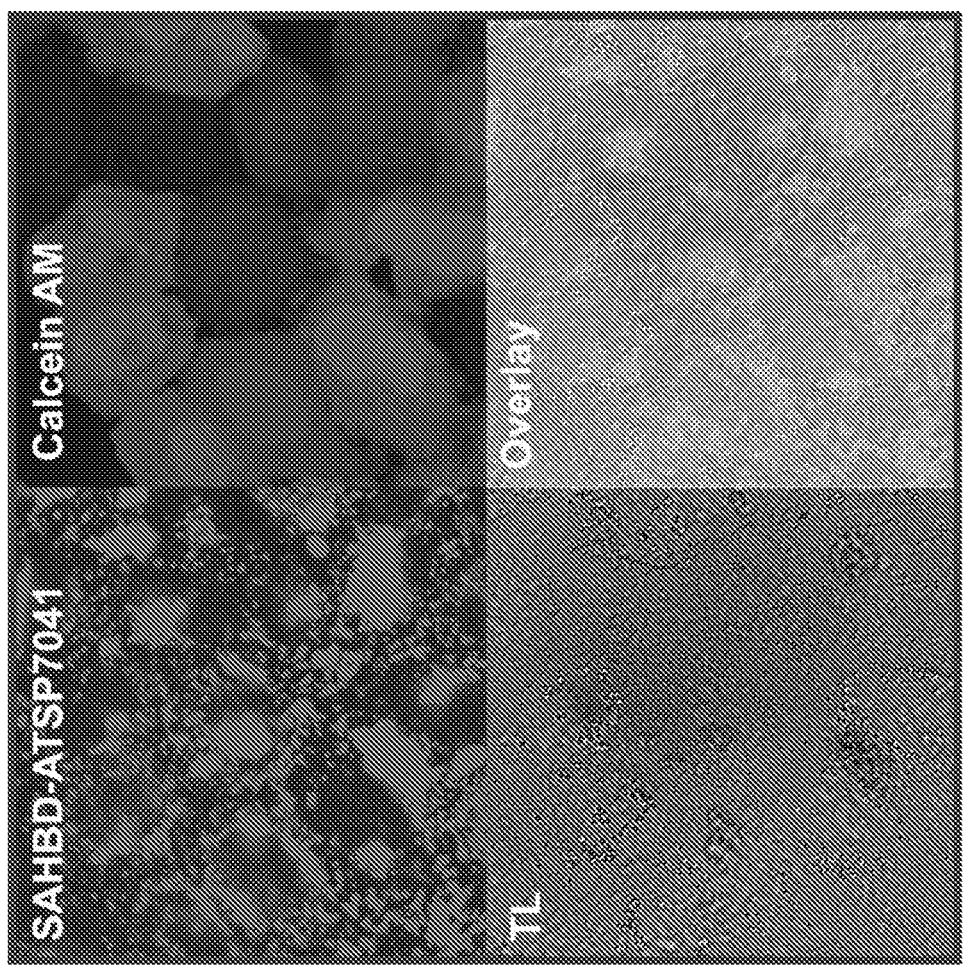
FIGS. 4A-4C. Enhanced uptake of an MCL-1 SAHB$_D$ stapled peptide upon conjugating to ATSP-7041, a bioactive CPSP.
Figure 4B:
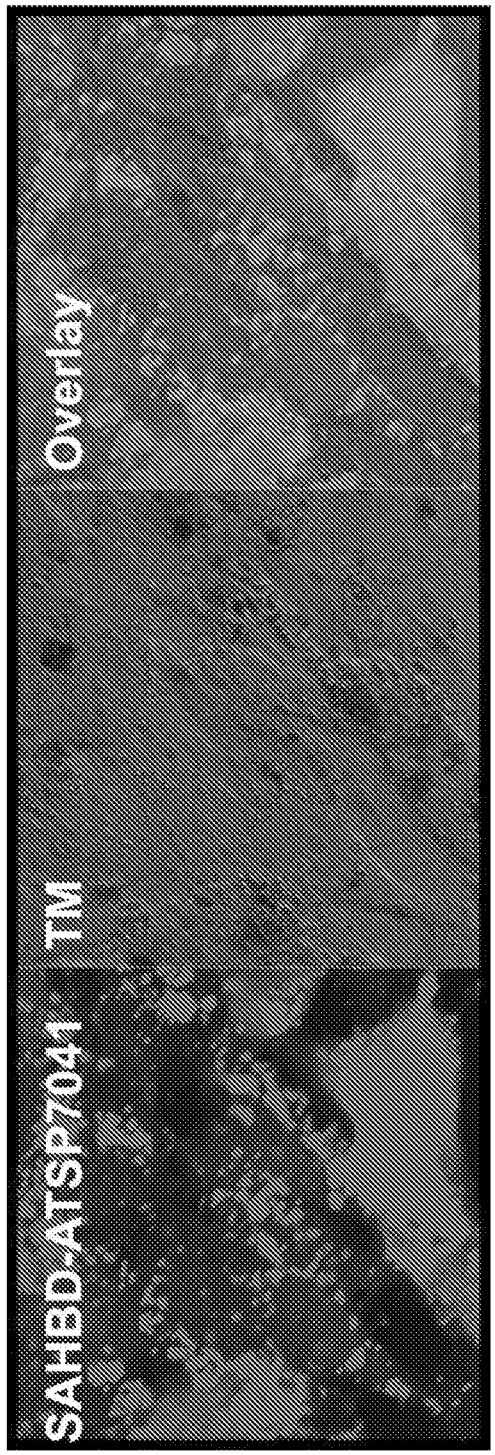
Figure 4C:
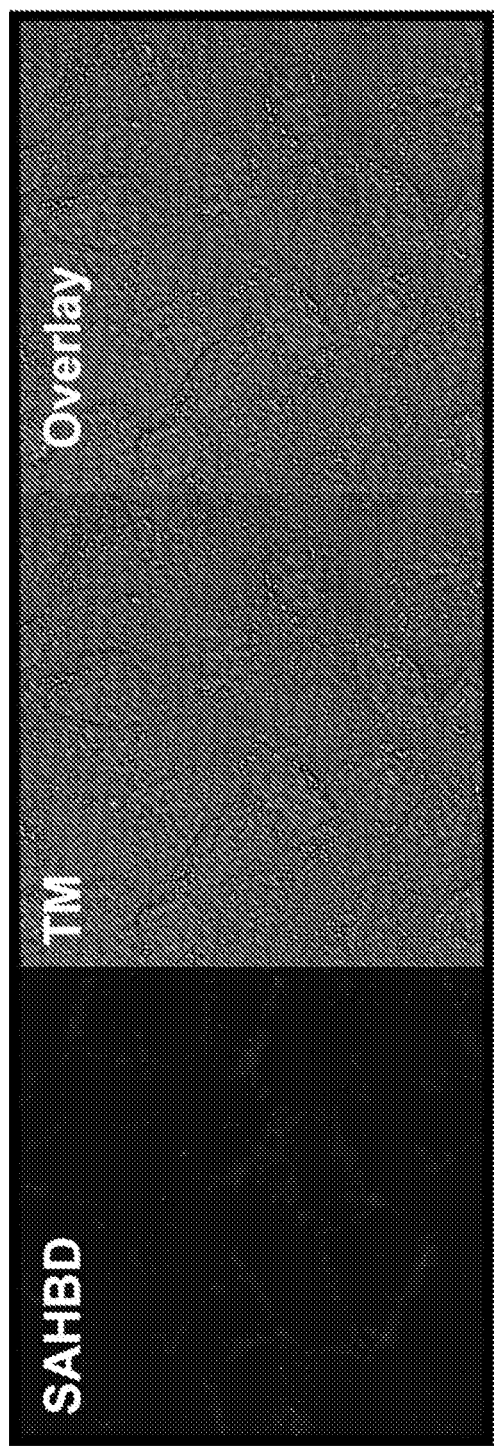
Figure 5:
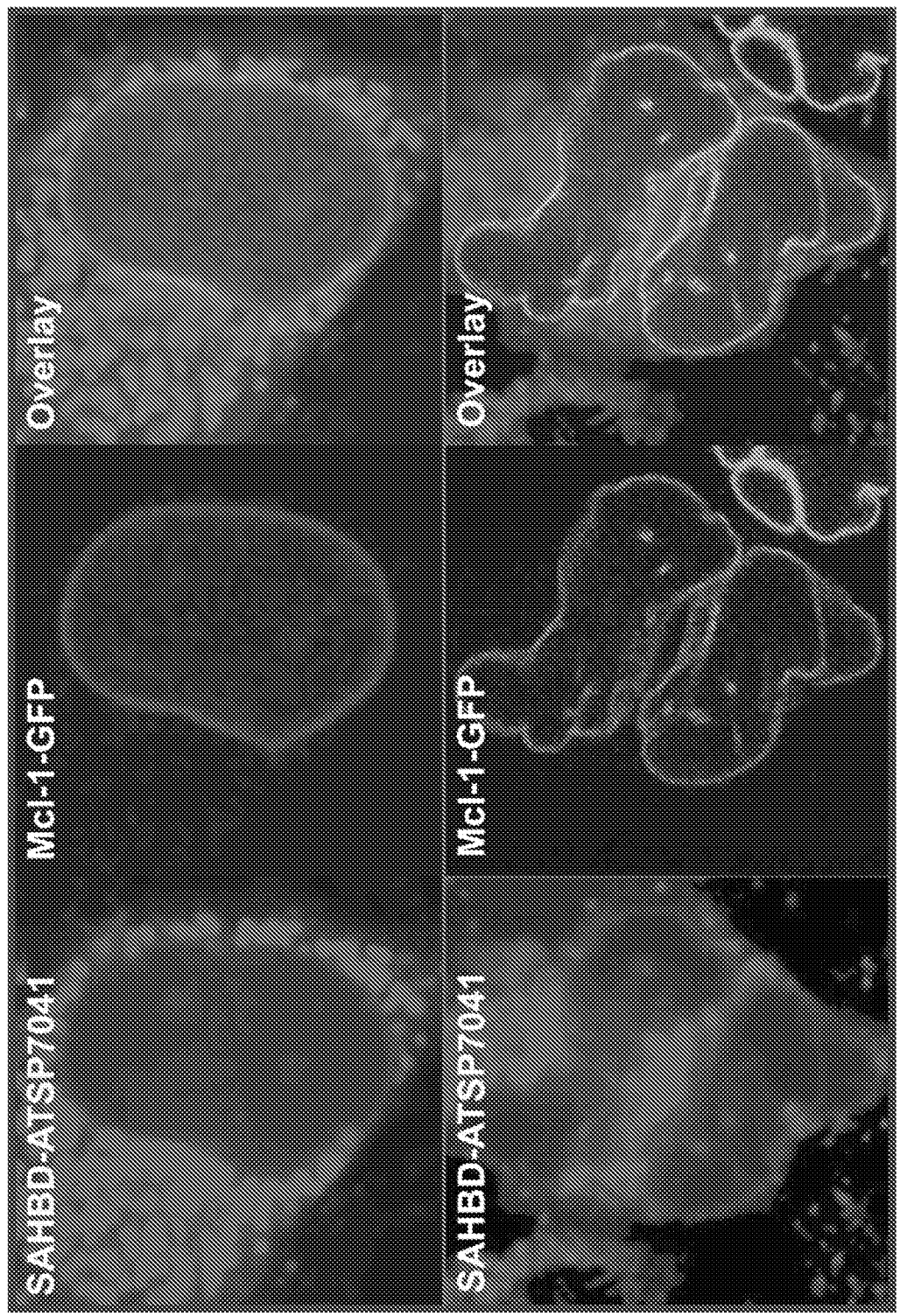
FIG. 5. The CPSP-MCL-1 SAHB$_D$ conjugate retains the capacity to engage its intracellular target, MCL-1, as demonstrated by the co-localization of CPSP-MCL-1 SAHB$_D$ with expressed MCL-1 that is ectopically targeted to the nuclear lamina.

As shown in FIG. 1 and FIGS. 4A-B, after incubating the TAMRA-labeled MCL-1 SAHB$_D$/ATSP-7041/fusion polypeptide (4 µM) with cells for 4 hours, the fusion polypeptide was efficiently delivered to the cytosol of treated cells, whereas exposure to TAMRA-labeled MCL-1 SAHB$_D$ alone (40 µM) showed relatively low cellular uptake (FIG. 4C) The capacity of TAMRA-labeled MCL-1 SAHB$_D$/ATSP-7041 fusion to maintain intracellular engagement of MCL-1 was demonstrated by the colocalization of the fusion to the nuclear lamina, where expressed MCL-1 was ectopically targeted (FIG. 5).

Figure 6:
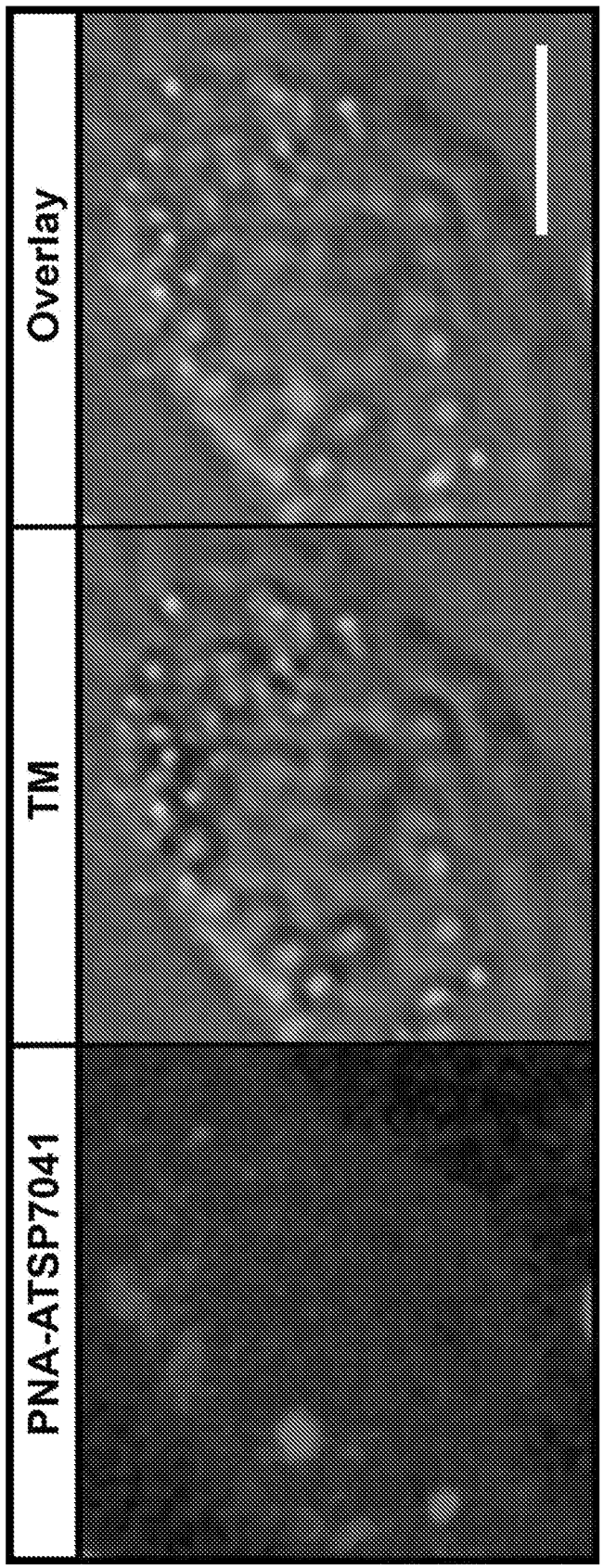
FIG. 6. Transport of an otherwise cell impermeable peptide nucleic acid into the cell upon fusion with CPSP3.

In another experiment, peptide nucleic acids are potential therapeutic modalities for targeting nucleic acid (i.e. antisense therapies), but their applications have been limited by poor cellular penetrance (Koppelhus et al., "Cellular delivery of peptide nucleic acid (PNA)." Advanced drug delivery reviews 55.2 (2003): 267-280; Zhao et al. "Delivery of cell-penetrating peptide-peptide nucleic acid conjugates by assembly on an oligonucleotide scaffold." Scientific reports 5 (2015): 17640). Here, ATSP-7041 was fused to a PNA (i.e., TAMRA-ATSP-7041/PNA in Table 2), resulting in its robust intracellular delivery (FIG. 6).

Figure 7:
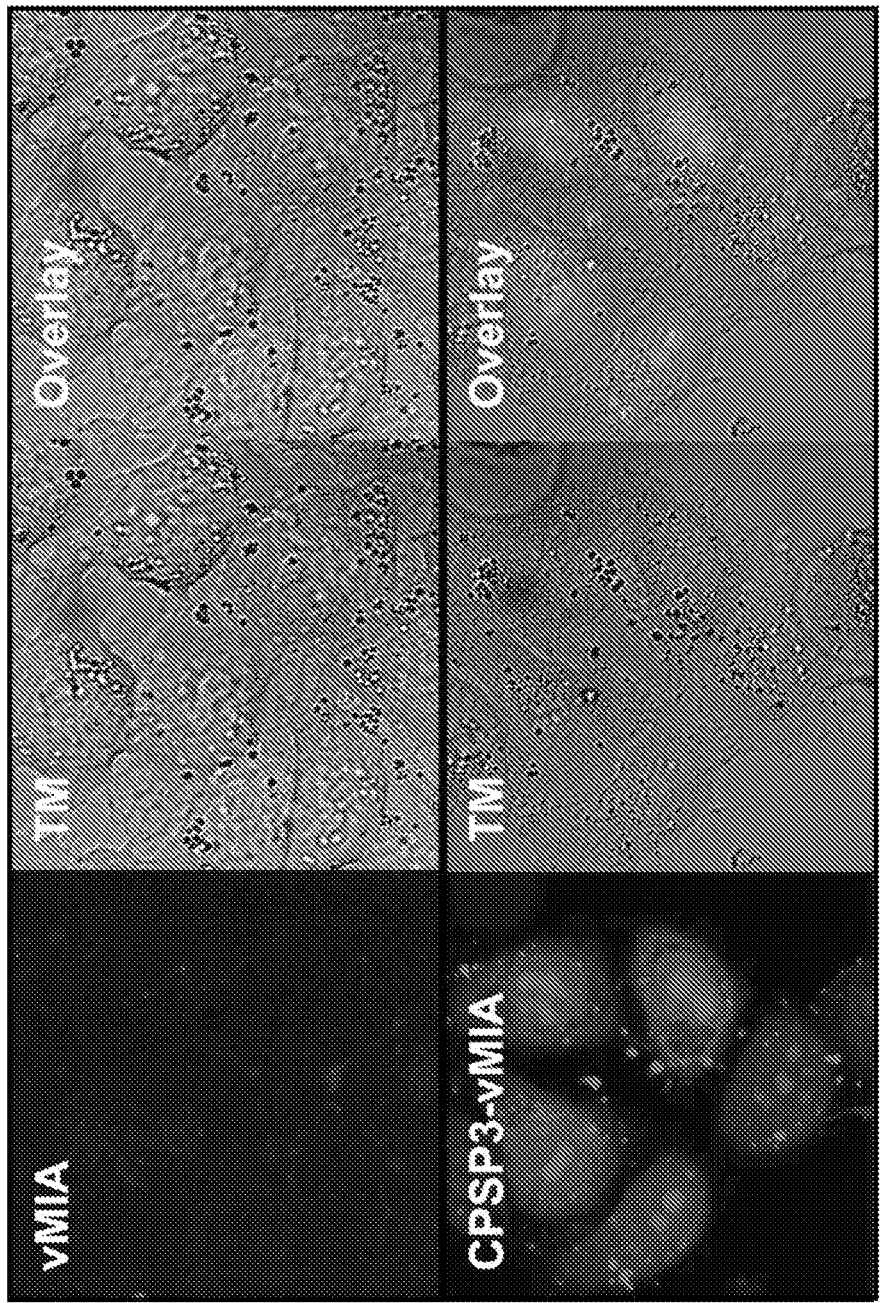
FIG. 7. Transport of an otherwise cell impermeable peptide into the cell upon fusion with CPSP3.

In addition, bioactive peptides are potential therapeutic modalities for targeting intracellular proteins, but their applications have been limited by minimal to no cellular penetrance. Here, an anti-apoptotic peptide derived from the CMV protein vMIA, which is otherwise cell impermeable (e.g. 40 µM, 4 h) (FIG. 7, top panel), was fused to CPSP3 (SEQ ID NO: 63), resulting in its robust intracellular delivery (e.g. 10 µM, 1 h) (FIG. 7, bottom panel).

Example 4: Design of CPSPs for Intracellular Delivery of Cargo

CPSPs are generated by installing non-natural amino acids bearing olefinic tethers (FIG. 8A) into peptide sequences at various locations along the length of the peptide, such as the (i, i+3), (i, i+4), (i, i+7) positions (FIG. 8B). Identification of optimal staple positions to achieve robust cellular uptake and cargo delivery is determined by staple scanning (FIG. 8C). Double and triple stapling and staple scanning (FIG. 9), in addition to stitching and stitch scanning (FIG. 10), are also employed to develop optimal CPSPs for cargo delivery into the cell.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A fusion polypeptide comprising:
   an internally cross-linked polypeptide comprising any one of the amino acid sequences: (i) $X_1R_2R_3R_2X_5R_2B$ (SEQ ID NO: 3), (ii) $X_1R_2R_3R_2X_5B$ (SEQ ID NO: 4), (iii) $X_1R_2R_2R_2X_5R_2B$ (SEQ ID NO: 7), (iv) $X_1R_2R_3R_2X_4R_2BGBR_2X_5R_2R_3R_2X_6$ (SEQ ID NO: 8), or (v) $X_1R_2R_3R_2X_4R_2BGX_5R_2R_3R_2X_6R_2B$ (SEQ ID NO: 9),
   wherein B is Norleucine;
   wherein $R_2$ is L-Arg; $R_3$ is D-Arg;
   wherein $X_1$, $X_4$, $X_5$, and $X_6$ are each (S)-2-(4'-pentenyl)alanine;
   wherein $X_1$ and $X_4$ and $X_5$ and $X_6$ are cross-linked, and wherein the internally cross-linked polypeptide is linked to a second moiety.

2. The fusion polypeptide of claim 1, wherein the second moiety comprises:
   (a) an scFv antibody, an scFv-Fc fusion, a dAb (domain antibody), a Fab, a Fab', a F(ab')2 fragment, a single chain antibody, or a minibody; and/or
   (b) a small molecule drug, a cytokine, an antioxidant, a nucleic acid, a peptide, a peptide nucleic acid (PNA), an antibody, a gene-editing or RNA-editing complex, a stapled peptide, a stitched peptide, or a protein.

3. A compound comprising an internally cross-linked polypeptide comprising any one of the amino acid sequences: (i) $X_1R_2R_3R_2X_5R_2B$ (SEQ ID NO: 3), (ii) $X_1R_2R_3R_2X_5B$ (SEQ ID NO: 4), (iii) $X_1R_2R_2R_2X_5R_2B$ (SEQ ID NO: 7), (iv) $X_1R_2R_3R_2X_4R_2BGBR_2X_5R_2R_3R_2X_6$ (SEQ ID NO: 8), or (v) $X_1R_2R_3R_2X_4R_2BGX_5R_2R_3R_2X_6R_2B$ (SEQ ID NO: 9),
   wherein B is Norleucine;
   wherein $R_2$ is L-Arg, $R_3$ is D-Arg;
   wherein $X_1$, $X_4$, $X_5$, and $X_6$ are each (S)-2-(4'-pentenyl)alanine; and
   wherein $X_1$ and $X_4$ and $X_5$ and $X_6$ are cross-linked, and a cargo.

4. The compound of claim 3, wherein the cargo is linked to the internally cross-linked polypeptide by a chemical linker or by a peptide linker.

5. The compound of claim 3, wherein the cargo comprises an scFv antibody, an scFv-Fc fusion, a domain antibody, a Fab, a Fab', a F(ab')$_2$ fragment, a single chain antibody, a monobody, a minibody, or a nanobody.

6. The compound of claim 3, wherein the cargo is:
   (a) a peptide, a stapled peptide, a small molecule, or an antibody or antigen-binding fragment thereof, or
   (b) an antioxidant, a nucleic acid, a peptide nucleic acid (PNA), an antibody, a gene-editing or RNA-editing complex, a protein, a cytokine, an anxiolytic agent, an anticonvulsant, a polynucleotide, or a cytotoxic agent.

7. A method of delivering an agent into a cell, the method comprising:
   contacting the cell with a compound comprising (1) the agent and (2) a cell-permeable stapled peptide, wherein the agent is linked to the cell-permeable stapled peptide, wherein the cell-permeable stapled peptide comprises an internally cross-linked polypeptide comprising any one of the amino acid sequences: (i) $X_1R_2R_3R_2X_5R_2B$ (SEQ ID NO: 3), (ii) $X_1R_2R_3R_2X_5B$ (SEQ ID NO: 4), (iii) $X_1R_2R_2R_2X_5R_2B$ (SEQ ID NO: 7), (iv) $X_1R_2R_3R_2X_4R_2BGBR_2X_5R_2R_3R_2X_6$ (SEQ ID NO: 8), or (v) $X_1R_2R_3R_2X_4R_2BGX_5R_2R_3R_2X_6R_2B$ (SEQ ID NO: 9),
   wherein B is Norleucine;
   wherein $R_2$ is L-Arg, $R_3$ is D-Arg;
   wherein $X_1$, $X_4$, $X_5$, and $X_6$ are each (S)-2-(4'-pentenyl)alanine; and
   wherein $X_1$ and $X_4$ and $X_5$ and $X_6$ are cross-linked.

8. The method of claim 7, wherein the agent is linked to the internally cross-linked polypeptide by a chemical linker or by a peptide linker.

9. The method of claim 7, wherein the agent is:
(a) an scFv antibody, an scFv-Fc fusion, a dAb (domain antibody), a Fab, a Fab', a F(ab')2 fragment, a single chain antibody, or a minibody,
(b) a stapled peptide, a stitched peptide, a small molecule, or an antibody or a fragment thereof, or
(c) an antioxidant, a nucleic acid, a peptide, a peptide nucleic acid (PNA), an antibody, a gene-editing or RNA-editing complex, a protein, a cytokine, an anxiolytic agent, an anticonvulsant, a polynucleotide, or a cytotoxic agent.

10. A method of administering an agent to a subject, the method comprising:
administering to a subject in need thereof a compound comprising (1) the agent and (2) a cell-permeable stapled peptide, wherein the agent is linked to the cell-permeable stapled peptide, wherein the cell-permeable stapled peptide comprises an internally cross-linked polypeptide comprising any one of the amino acid sequences: (i) $X_1R_2R_3R_2X_5R_2B$ (SEQ ID NO: 3), (ii) $X_1R_2R_3R_2X_5B$ (SEQ ID NO: 4), (iii) $X_1R_2R_2R_2X_5R_2B$ (SEQ ID NO: 7), (iv) $X_1R_2R_3R_2X_4R_2BGBR_2X_5R_2R_3R_2X_6$ (SEQ ID NO: 8), or (v) $X_1R_2R_3R_2X_4R_2BGX_5R_2R_3R_2X_6R_2B$ (SEQ ID NO: 9),
wherein B is Norleucine;
wherein $R_2$ is L-Arg, $R_3$ is D-Arg;
wherein $X_1$, $X_4$, $X_5$, and $X_6$ are each (S)-2-(4'-pentenyl) alanine; and
wherein $X_1$ and $X_4$ and $X_5$ and $X_6$ are cross-linked.

11. The method of claim 10, wherein the agent is linked to the internally cross-linked polypeptide by a chemical linker or by a peptide linker.

12. The method of claim 10, wherein the agent is:
(a) an scFv antibody, an scFv-Fc fusion, a dAb (domain antibody), a Fab, a Fab', a F(ab')2 fragment, a single chain antibody, or a minibody,
(b) a stapled peptide, a stitched peptide, a small molecule, or an antibody or a fragment thereof, or
(c) an antioxidant, a nucleic acid, a peptide, a peptide nucleic acid (PNA), an antibody, a gene-editing or RNA-editing complex, a protein, a cytokine, an anxiolytic agent, an anticonvulsant, a polynucleotide, or a cytotoxic agent.

13. An internally cross-linked polypeptide comprising any one of the amino acid sequences: (i) $X_1R_2R_3R_2X_5R_2B$ (SEQ ID NO: 3), (ii) $X_1R_2R_3R_2X_5B$ (SEQ ID NO: 4), (iii) $X_1R_2R_2R_2X_5R_2B$ (SEQ ID NO: 7), (iv) $X_1R_2R_3R_2X_4R_2BGBR_2X_5R_2R_3R_2X_6$ (SEQ ID NO: 8), or (v) $X_1R_2R_3R_2X_4R_2BGX_5R_2R_3R_2X_6R_2B$ (SEQ ID NO: 9),
wherein B is Norleucine;
wherein $R_2$, is L-Arg; $R_3$ is D-Arg;
wherein $X_1$, $X_4$, $X_5$, and $X_6$ are each (S)-2-(4'-pentenyl) alanine; and
wherein $X_1$ and $X_4$ and $X_5$ and $X_6$ are cross-linked.

14. The internally cross-linked polypeptide of claim 13, wherein the internally cross-linked polypeptide is fused to an agent, wherein the agent is selected from the group consisting of an scFv antibody, an scFv-Fc fusion, a dAb, a Fab, a Fab', a F(ab')2 fragment, a single chain antibody, a minibody, a small molecule drug, a cytokine, an antioxidant, a nucleic acid, peptide, a peptide nucleic acid, an antibody, a gene-editing or RNA-editing complex, a stapled peptide, a stitched peptide, and a protein.

15. The internally cross-linked polypeptide of claim 13, wherein the internally cross-linked polypeptide is attached to a cargo, and wherein the cargo is linked to the internally cross-linked polypeptide by a chemical linker or by a peptide linker.

16. The internally cross-linked polypeptide of claim 15, wherein the cargo comprises an scFv antibody, an scFv-Fc fusion, a dAb (domain antibody), a Fab, a Fab', a F(ab')2 fragment, a single chain antibody, a monobody, a minibody, or a nanobody.

17. The internally cross-linked polypeptide of claim 15, wherein the cargo is a peptide, a stapled peptide, a small molecule, an antibody or antigen-binding fragment thereof, an antioxidant, a nucleic acid, a peptide nucleic acid (PNA), an antibody, a gene-editing or RNA-editing complex, a protein, a cytokine, an anxiolytic agent, an anticonvulsant, a polynucleotide, or a cytotoxic agent.

18. A method of administering an agent to a subject, the method comprising
administering to a subject in need thereof a compound comprising (1) the agent and (2) the internally cross-linked polypeptide of claim 13.

19. The method of claim 18, wherein the subject is a human subject.

20. The internally cross-linked polypeptide of claim 14, wherein the amino acid sequence is $X_1R_2R_3R_2X_5R_2B$ (SEQ ID NO: 3),
wherein B is Norleucine;
wherein $R_2$, is L-Arg; $R_3$ is D-Arg;
wherein $X_1$, $X_4$, $X_5$, and $X_6$ are each (S)-2-(4'-pentenyl) alanine; and
wherein $X_1$ and $X_4$ and $X_5$ and $X_6$ are cross-linked.

21. The internally cross-linked polypeptide of claim 14, wherein the amino acid sequence is $X_1R_2R_3R_2X_5B$ (SEQ ID NO: 4),
wherein B is Norleucine;
wherein $R_2$, is L-Arg; $R_3$ is D-Arg;
wherein $X_1$, $X_4$, $X_5$, and $X_6$ are each (S)-2-(4'-pentenyl) alanine; and
wherein $X_1$ and $X_4$ and $X_5$ and $X_6$ are cross-linked.

22. The internally cross-linked polypeptide of claim 14, wherein the amino acid sequence is $X_1R_2R_2R_2X_5R_2B$ (SEQ ID NO: 7),
wherein B is Norleucine;
wherein $R_2$, is L-Arg; $R_3$ is D-Arg;
wherein $X_1$, $X_4$, $X_5$, and $X_6$ are each (S)-2-(4'-pentenyl) alanine; and
wherein $X_1$ and $X_4$ and $X_5$ and $X_6$ are cross-linked.

23. The internally cross-linked polypeptide of claim 14, wherein the amino acid sequence is $X_1R_2R_3R_2X_4R_2BGBR_2X_5R_2R_3R_2X_6$ (SEQ ID NO: 8),
wherein B is Norleucine;
wherein $R_2$, is L-Arg; $R_3$ is D-Arg;
wherein $X_1$, $X_4$, $X_5$, and $X_6$ are each (S)-2-(4'-pentenyl) alanine; and
wherein $X_1$ and $X_4$ and $X_5$ and $X_6$ are cross-linked.

24. The internally cross-linked polypeptide of claim 14, wherein the amino acid sequence is $X_1R_2R_3R_2X_4R_2BGX_5R_2R_3R_2X_6R_2B$ (SEQ ID NO: 9),
wherein B is Norleucine;
wherein $R_2$, is L-Arg; $R_3$ is D-Arg;
wherein $X_1$, $X_4$, $X_5$, and $X_6$ are each (S)-2-(4'-pentenyl) alanine; and
wherein $X_1$ and $X_4$ and $X_5$ and $X_6$ are cross-linked.

* * * * *